United States Patent
Deutsch

(10) Patent No.: US 9,227,024 B2
(45) Date of Patent: Jan. 5, 2016

(54) SYSTEMS AND METHODS FOR MONITORING CONTACT WITH PATIENT'S CATHETER ASSEMBLY

(76) Inventor: Richard Deutsch, Raleigh, NC (US)

( * ) Notice: Subject to any disclaimer, the term of this patent is extended or adjusted under 35 U.S.C. 154(b) by 813 days.

(21) Appl. No.: 13/507,189

(22) Filed: Jun. 12, 2012

(65) Prior Publication Data

US 2012/0316497 A1 Dec. 13, 2012

Related U.S. Application Data

(60) Provisional application No. 61/520,637, filed on Jun. 13, 2011.

(51) Int. Cl.
| | |
|---|---|
| *A61M 5/50* | (2006.01) |
| *A61M 39/18* | (2006.01) |
| *A61M 25/00* | (2006.01) |

(52) U.S. Cl.
CPC .......... *A61M 5/5086* (2013.01); *A61M 25/0017* (2013.01); *A61M 39/18* (2013.01)

(58) Field of Classification Search
CPC .......... A61M 5/5086; A61M 25/0017; A61M 39/18; A61M 2205/33; A61M 2205/18; A61M 2205/02; A61M 5/16831; A61M 2005/1726; A61M 5/168; C12Q 1/18; G01N 27/00; G01N 27/30; B01L 2300/0645; B82Y 30/00
USPC ............ 600/309, 345, 301, 346; 604/111, 67
See application file for complete search history.

(56) References Cited

U.S. PATENT DOCUMENTS

| | | | | |
|---|---|---|---|---|
| 6,319,242 B1 * | 11/2001 | Patterson et al. | ............. | 604/508 |
| 6,469,524 B1 * | 10/2002 | Oberdier | ........................ | 324/688 |
| 6,724,324 B1 * | 4/2004 | Lambert | ........................ | 341/33 |
| 2009/0163904 A1 * | 6/2009 | Miller et al. | .................... | 606/33 |

* cited by examiner

*Primary Examiner* — Manuel Mendez

(57) ABSTRACT

One or more intravenous catheter assemblies are monitored to ensure compliance with required hygienic procedures and/or to ensure only persons who have properly sanitized their hands are allowed to attend to such catheter assemblies. Detecting electrodes incorporated as part of such catheter assemblies facilitate determination as to whether potential contamination may have occurred. The hygienic status of a health care worker attending to the catheter assembly, as possibly evidenced by detected use of a sanitizer, may be used to determine whether the catheter assembly is being subjected to contamination.

16 Claims, 21 Drawing Sheets

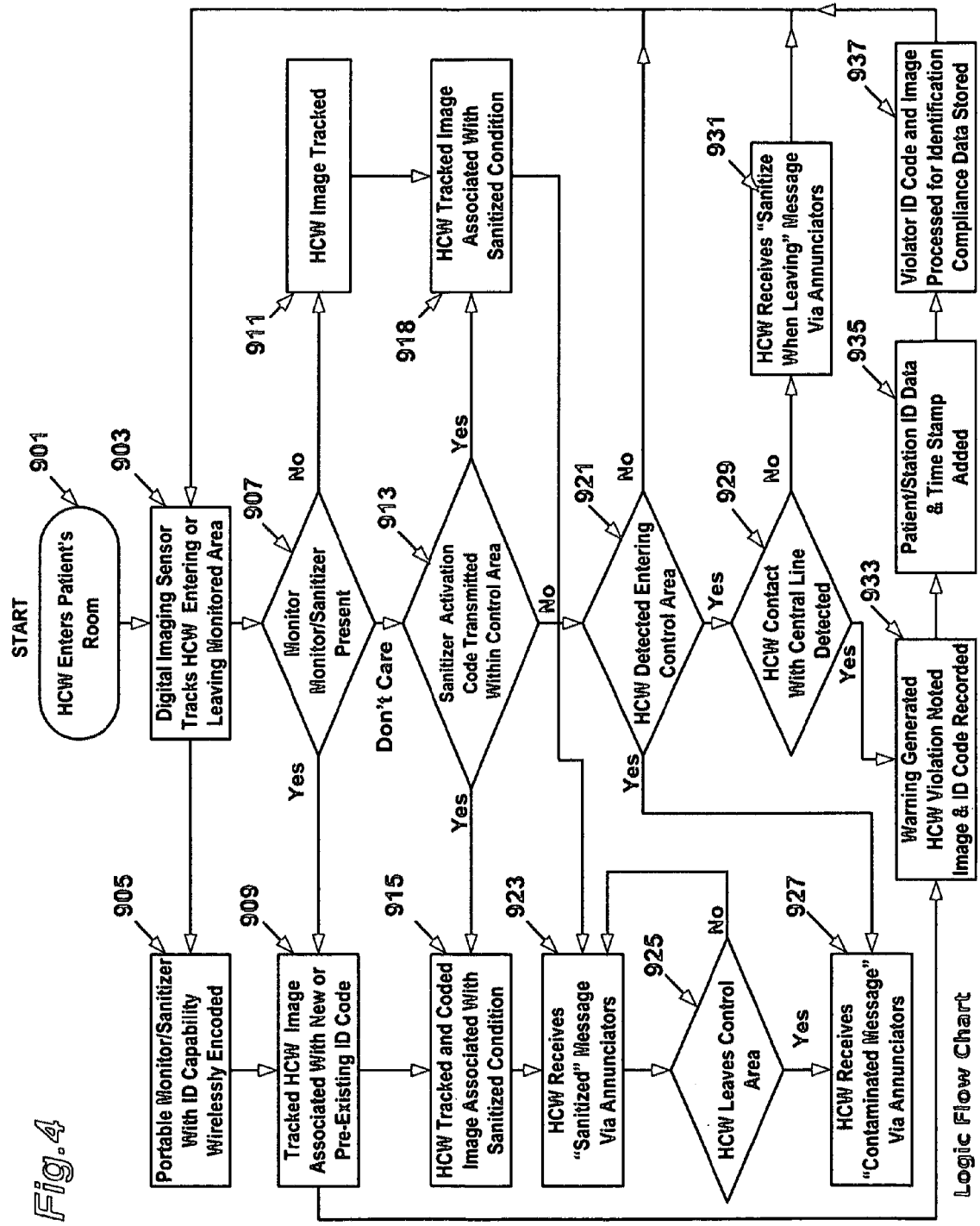

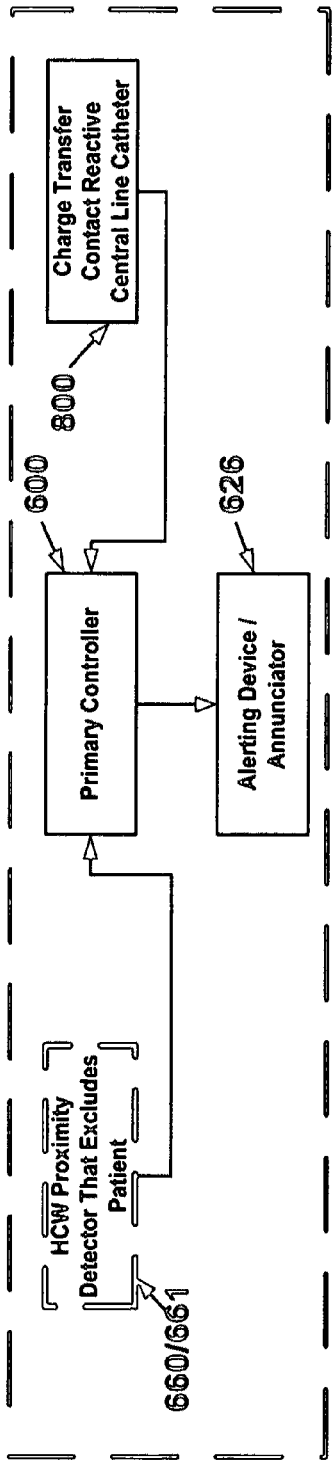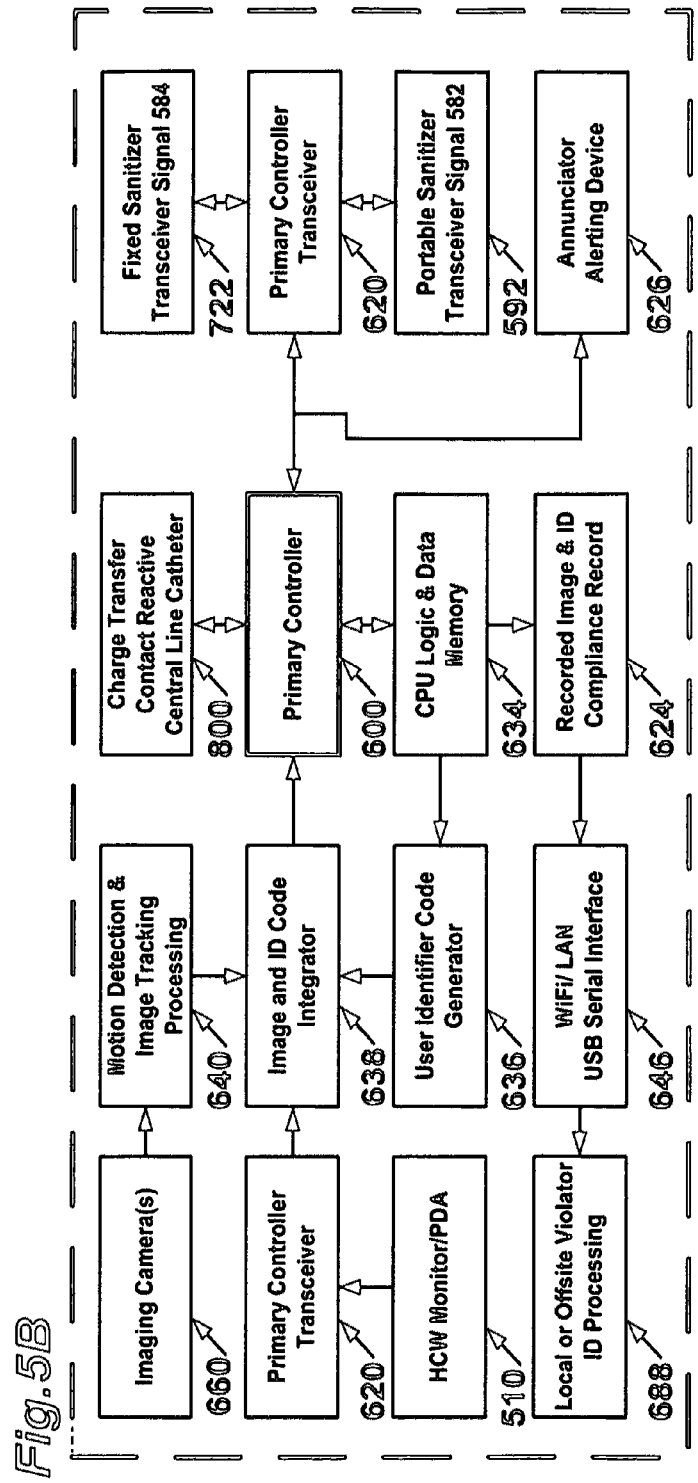

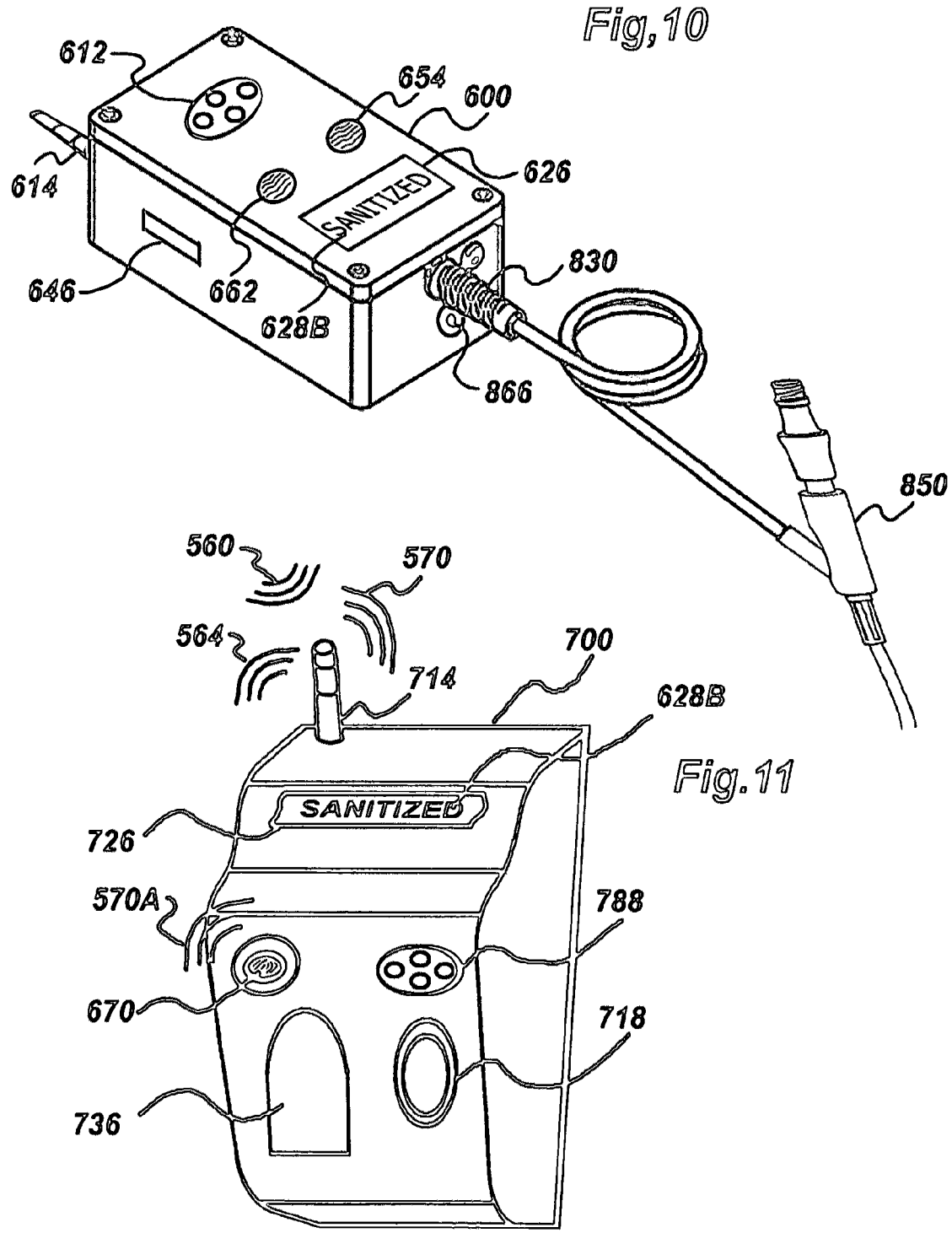

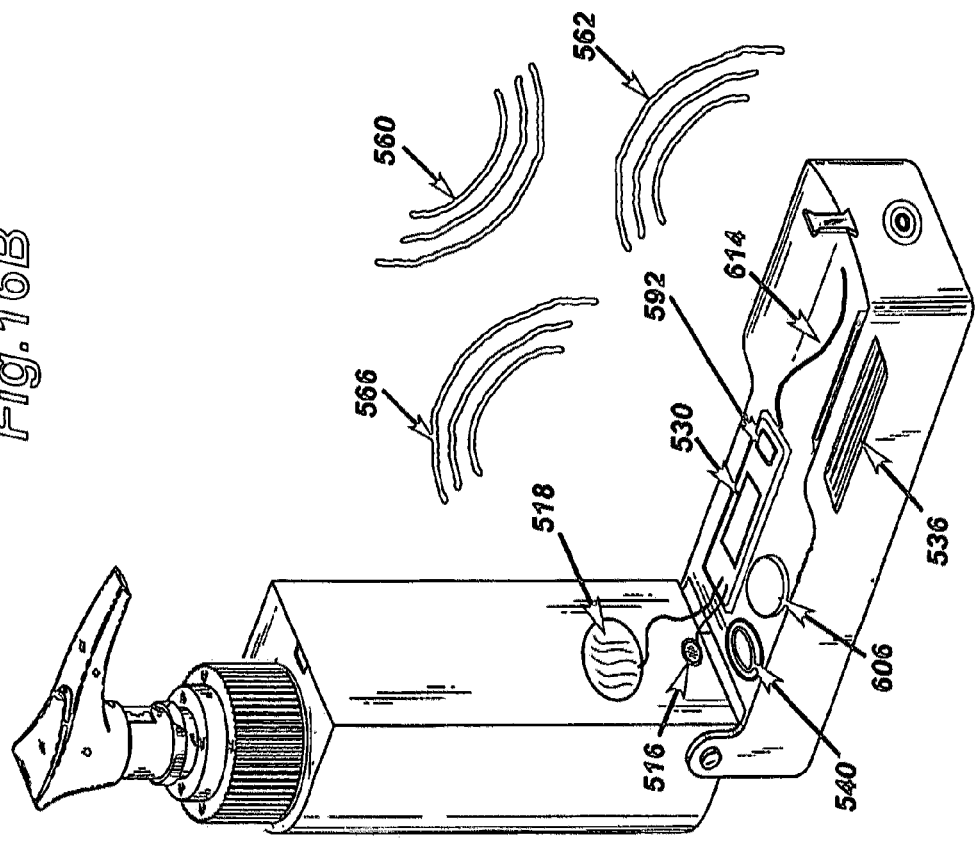
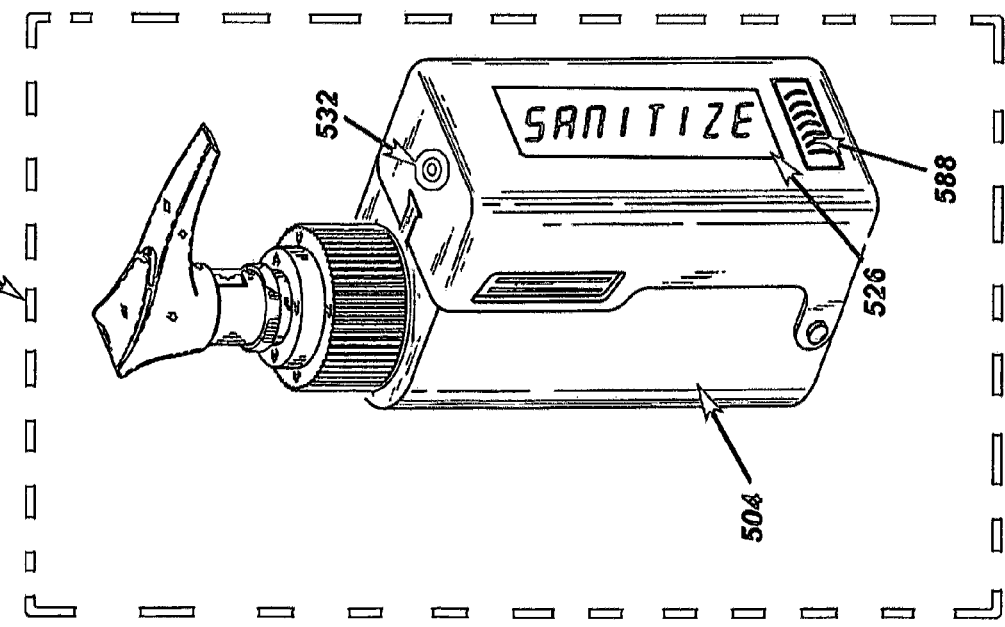

SYSTEMS AND METHODS FOR MONITORING CONTACT WITH PATIENT'S CATHETER ASSEMBLY

CROSS-REFERENCE TO RELATED APPLICATION

This application claims the benefit of U.S. Provisional Application No. 61/520,637 filed on Jun. 13, 2011.

BACKGROUND OF THE INVENTION

1. Field of the Invention

The field of the invention relates to systems and methods for monitoring health care workers' compliance with required hand hygiene practices when installing and/or utilizing a catheter assembly (intravenous venous catheter) associated with patients who may be adversely affected by non-sanitized health-care workers.

2. Brief Description of the Related Art

The Center for Disease Control, advocates there are over 2 million preventable healthcare-associated infections (HAIs) occurring each year in U.S. Hospitals resulting in billions of dollars in additional healthcare costs. The primary source of the majority of deaths from these infections is Central Line Associated Bloodstream Infections (CLBSI's). CLBSI's are considered preventable by the CDC through proper hand hygiene and sanitary management of the intravenous catheter.

An intravenous catheter (also known as a central line catheter) is a catheter (tube) that doctors often place in a large vein in the neck, chest or groin to give medication or fluids or to collect blood for medical tests. Intravenous catheters may also be known as IV's that are frequently used to give medicine or fluids into a vein near the skins surface (usually on the arm or hand), for short periods of time. Central lines catheters are commonly used in intensive care units as intravenous catheters used to access a major vein that is close to the heart and can remain in place for weeks or months. All patient associated catheters to include but not limited to Intravenous catheters, Central line catheters, Indwelling catheters, IV lines, and PICC (Peripherally Inserted Catheter) lines are to be considered the same regarding the scope of this application. In addition, Folly catheters, medical drains and physiologic catheters to include intravenous lines for adding or removing bodily fluids are to be included in the intent of providing a means for monitoring hygiene and contact with patient catheters and are intended to fall within the scope of this art.

U.S. Pat. No. 6,882,278 describes another system that monitors compliance with recommended hand-washing practices. The system includes a hand-washing detector and an event detector such as a motion detector that detects an event such a person entering or leaving a room. A control unit determines whether a person has washed his hands within a predetermined time period before entering the room.

U.S. Pat. Nos. 6,727,818 and 6,975,231 disclose other systems for promoting hygienic practices. The first mentioned patent discloses a system that tracks the movements of health care workers throughout the facility and within a patient's room. The health care workers are provided with badges that transmit ID information to sensors located in the hallways and rooms of the facility, which in turn transmit location information to a master station. ID information is also transmitted to wash sink sensors to indicate whether the health care worker has washed his hands. If the health care worker enters a patient contact zone in the patient's room without having complied with the required hand washing procedure, an alert is provided by the health care worker's badge and/or other alerting devices located on the patient's bed or in the patient's room.

A time delay may be employed before a warning alert is provided so that an alert is not triggered by a health care worker who is only briefly in the patient contact zone. U.S. Pat. No. 6,975,231 discloses a system employing sets of detectors located just outside and within a patient's room. These detectors are actuated sequentially as a person enters the room and the time between their actuation is monitored in determining whether a person has entered the room. A determination is made as to whether the person has washed his hands within a predetermined period of time, and a warning signal is generated if the hands have not been washed within the set period.

U.S. Pat. No. 8,090,155 Lacey discloses the use of a camera to monitor the hands so as to determine hand washing activity but does not provide a means to address the issue of identifying whose hands are being monitored and their relationship to the patient.

U.S. Pat. Nos. 2011/027740, 8,110,047 8,094,029, 20050248461, 8,085,155, 7,898,407, 7,855,651, 7,818,083 7,682,464, 7,605,704, 7,375,640 and 7,372,367 hygiene monitoring schemes all require the use of RFID badges. The application of RFID as the backbone of almost all currently available hygiene monitoring systems ignores the restrictive nature presented by this technology. RFID limitations become apparent when considering the absence of an RFID badge being carried by a caregiver, Health Care Worker or visitor allows the potential hygiene violator to then become invisible to the associated monitoring system. The use of radio waves opposed to digital imaging as a means of determining location and proximity, are subject to inconsistencies in ranging dependent on many outside variables, particularly in a RF "noisy" hostile hospital environment. Radiating in a fixed circular or elliptical pattern, the application of such radio waves or IR beams opposed to digital imaging for near proximity monitoring is extremely limited in resolving "the finite point of care", the actual probable contamination point between the HCW or visitor and the patient's medical devices.

SUMMARY OF THE INVENTION

A system provided in accordance with one exemplary embodiment includes a catheter assembly including one or more tubes for conveying fluids. The system further includes a charge transfer proximity sensor assembly comprising an electrode coupled to the catheter assembly and a charge transfer controller circuit electrically connected to the electrode. The charge transfer proximity sensor assembly is configured to detect contact or near contact by a person with the catheter assembly configured to add or remove fluids to/from a patient and generate an electrical signal responsive to such contact or near contact.

A system in accordance with another exemplary embodiment includes a liquid source, a catheter assembly including one or more tubes for conveying fluid and in fluid communication with the liquid source, and a controller electrically coupled to the catheter assembly, the controller being configured to detect a change in an electrical parameter resulting from a person's contact with or close proximity to the catheter assembly and generate a signal upon detection of the change in the electrical parameter.

A method in accordance with an exemplary embodiment includes detecting whether a person is within a selected area by using a digital imaging device, detecting whether an electrical signal has been generated by a hand sanitizer evidencing use of the hand sanitizer while the person is within the selected area, electronically detecting whether the person has made contact or near contact with a patient's catheter assembly, identifying that person and generating a signal representing non-compliance if contact or near contact with the catheter assembly is electronically detected without prior generation of the electrical signal from the hand sanitizer.

A further exemplary method includes detecting a change in an electrical parameter resulting from contact or near contact by a person with a catheter assembly connected between a liquid source and a patient, and actuating an annunciator responsive to detection of the change in the electrical parameter.

A further exemplary method includes detecting a change in an electrical parameter resulting from contact or near contact by a person with a catheter assembly connected between a liquid source and a patient, and actuating an annunciator responsive to detection of the change in the electrical parameter.

A further exemplary method includes detecting contact or near contact with a patient's catheter by a person via an electrode assembly capable of detection of the change in an electrical parameter. The electrode assembly may be integral or removable secured to the catheter so as to be operatively associated with the patient's catheter as a means of imparting contact or proximity detection to the catheter.

BRIEF DESCRIPTION OF THE DRAWINGS

FIG. 4 is a flow diagram illustrating the logic process of detection, tracking identification and monitoring the intravenous catheter contact and hygiene actions of a health care worker by a catheter monitoring system;

FIG. 5A is a flow diagram of a basic catheter hygiene monitoring system with an optional motion detection sensor;

FIG. 5B is a flow diagram of the communication tree of the primary components of a catheter hygiene monitoring system;

FIG. 10 is a diagrammatic illustration of a primary controller electrically connected to a contact sensor incorporated with an intravenous catheter assembly;

FIG. 11 is a diagrammatic illustration of a fixed base sanitizer dispenser operatively associated and usable with a catheter hygiene monitoring system;

FIG. 16A is a diagrammatic view showing a portable monitor/sanitizer dispenser in a closed position;

FIG. 16B is a diagrammatic illustration of a portable monitor/sanitizer dispenser assembly in an open position;

DETAILED DESCRIPTION OF THE PREFERRED EMBODIMENTS

Figure 1:
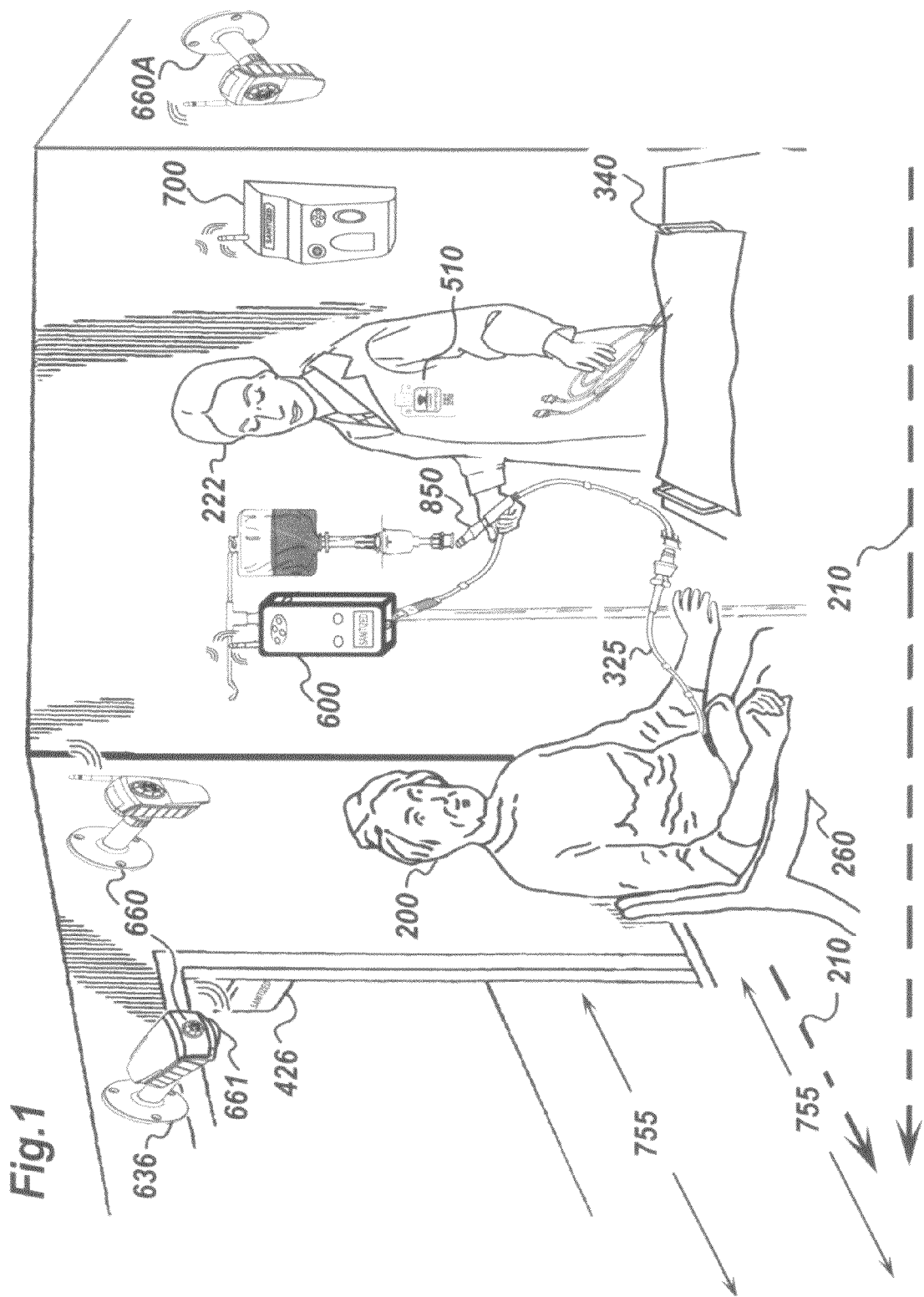
FIG. 1 is a perspective view showing a hospital room, a patient, a health care worker and an intravenous catheter hygiene monitoring system in accordance with the invention.

An exemplary method according to the invention includes detecting with a contact sensor whether a person's hand, such as a health care worker's (HCW) hand, is in close proximity to or in contact with a patient's intravenous catheter, commonly referred to, though not exclusively as a Central Line, CVC, CVC line, IV line, PICCS, Primary line, PIV, Hickman line, Indwelling line, Percutaneous Line or Mid Line (these terms to be used interchangeably within this art). Alternately, a physiologic catheter such as a Folly catheter, used for removing bodily fluids is to be considered part of this description as well. The term "close proximity" may be defined as being 25 cm. or less to a sensor, such as a detection electrode, or an intravenous catheter assembly electrically associated with a detection electrode. One or more embodiments of the exemplary method further include reminding the HCW or patient visitor (these terms to be used interchangeably for this art) to sanitize their hands prior to contacting the patient's intravenous catheter via an annunciator when hand contact with the patient's intravenous catheter is determined to be imminent. Since a patient's intravenous catheter is not ordinarily in danger of contamination unless actually touched by an HCW or other person, the use of a charge transfer touch sensor as a contact detector helps ensure that the HCW is typically not considered to have violated hygiene protocol unless he/she has actually touched a patient's intravenous catheter without having sanitized his/her hands in near proximity (preferably <2 meters) and immediately prior to such contact. A contact detector, a digital counter, a timing device, a location device preferably an imaging device and optionally, a monitoring badge may be employed to record and determine the identity of the Health Care Worker each time a system associated sanitizer is used and when a HCW is specifically compliant or noncompliant with hygiene protocol when interacting with a patient's intravenous catheter.

Detection of a person in close proximity to the patient's intravenous catheter or determination of their hygiene status does not necessarily require the wearing of a monitor or other transmitting device. Accordingly, a person who is not wearing a monitor may be determined to be compliant or non-compliant reflecting whether or not he has sanitized his hands if he comes in close proximity to or contacts a patient's intravenous catheter and has or has not activated a system associated sanitizer or system associated sanitizer detector. The system preferably provides a data recording system including but not limited to Wi-Fi enabled video camera or digital imaging system or other data collection means, for recording and compiling information on any compliant or non-compliant person who comes into close proximity to or in contact with a patient's intravenous catheter, whether such non-compliance of protocol is a result of not following required hygienic procedures and/or not wearing an appropriate monitor.

An exemplary system for promoting hygienic practices includes an intravenous catheter device such as a hub or an interconnection or an IV port or needle or the like operatively associated with a charge transfer contact sensor. The sensor is associated with the intravenous catheter device by being incorporated on or electrically associated with one or more components of the catheter device such that it can detect a HCW's hand in close proximity thereto or possibly contacting the intravenous catheter. An indicator is operatively associated with the sensor. In the preferred embodiment, the sensor is at least partially mounted to the catheter. In a more specific and preferred embodiment, means are provided for generating a first signal only when an additional sensor has detected a HCW in near proximity to the patient. A sanitizing device such as a sanitizer dispenser either fixed or portable, a sink, and a soap dispenser, with or without a sink, is employed within the preferred system. Preferably, a means is provided for generating a second signal when the sanitizing device is actuated within a monitored area in near proximity to the patient. The second signal can be generated when, for example, soap is dispensed, water flows in the sink or some other activity associated with hand sanitizing occurs. The indicator device may be incorporated in a monitor worn by the HCW or provided as a display located near the patient. A processing assembly determines whether the second signal that results from actuation of the sanitizing device has been generated and causes the actuation of the indicator device if the second signal has not been generated and the proximity sensor has detected the presence of a HCW in near proximity to the patient. If the system requires or permits use of a sanitizer/monitor worn or carried by the health care worker, the indicator device can be actuated should the worker or other person be detected in close proximity to the patient intravenous catheter without such a monitor. The system can be programmed, in certain circumstances, to detect whether the health care worker has used a glove and gown dispenser before coming into near proximity to a patient as described by U.S. Publication No. 2011/0007950, which is incorporated by reference herein. Such dispensers may be provided to provide additional hygiene precautions to protect the patient and the HCW and can be considered sanitizing devices for the purposes of this application.

A system for monitoring patients is further provided that can be used to enhance patient safety and/or hygiene. The system may include first and second detectors as described by U.S. Pat. No. 7,893,842, incorporated by reference herein. A patient hygiene monitoring system is also provided that requires contact or near contact with a patient intravenous catheter by a HCW in order for a signal to be generated. An indicator device is operatively associated with a proximity sensor in such a system. In a preferred embodiment, the system employs a charge transfer sensor that is operatively associated with detection of contact with the intravenous catheter assembly. The system may further include a sanitizing device and a processing assembly configured to determine whether the person contacting the critical components of the intravenous catheter assembly has used the sanitizing device. A monitor may also be provided as part of the system, in which case the processing assembly is configured to determine the identity of and/or whether the HCW contacting the patient's intravenous catheter is wearing a monitor.

Figure 12:
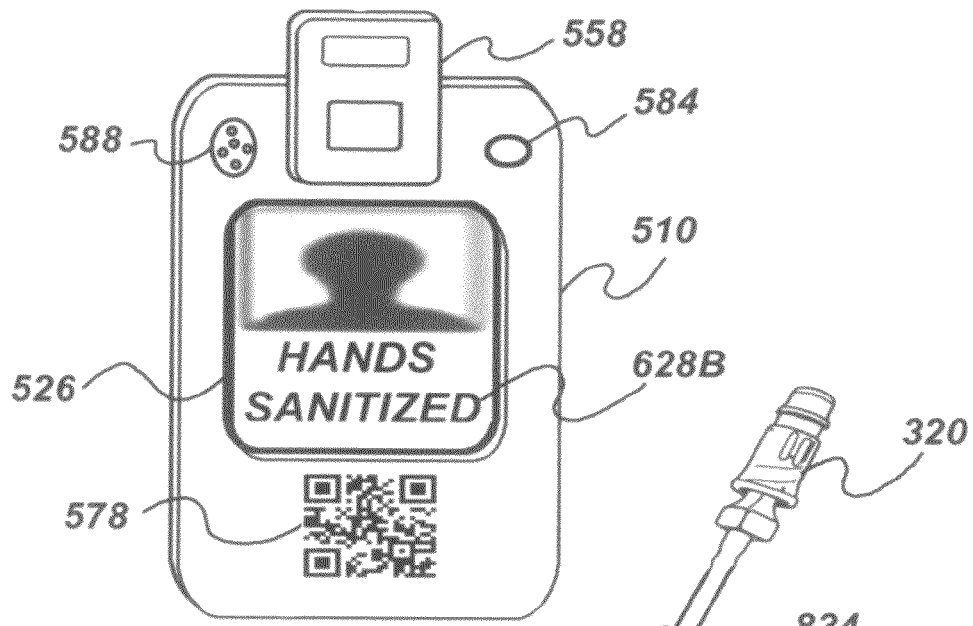
FIG. 12 is a diagrammatic view of a monitor adapted and operatively associated with a catheter hygiene monitoring system to be worn by a health care worker or visitor that includes optical QR identification coding.

A primary controller is provided that is capable of communicating with one or more digital imaging devices associated with an electro-optical motion detection person tracking system, integrating one or more intravenous catheter contact sensors and a co-operating fixed base sanitizer dispenser, both capable of wireless bi-directional communication with the primary controller. A monitor may be provided to be worn by the healthcare worker. The monitor is capable of bi-directional communication with the primary controller and functions as a means of indicating and associating the hygiene status of the caregiver bearing such monitor with their tracked image. Additional capabilities of the monitor include the ability to remotely provide identification information associated with the healthcare worker upon interrogation by the primary controller or the sanitizer. A primary controller causes a low power signal to be transmitted to the monitor, causing the status of the monitor to change to "contaminated", when the Health Care Worker or visitor is detected entering or leaving the patient control area (an area preferably within 2 meters surrounding the patient) as determined by a HCW digital imaging location and tracking detector and associated image processing. Detection and determination of the HCW's location via tracking sensors and actuation of an associated sanitizing device within a patient control area may be required to cause a low power signal to be generated to change the monitor display to "sanitized". The elements comprising the HCW monitor are common to those of other monitors and controllers discussed below and the same reference numerals are accordingly employed to designate them. It is preferable though not required to operate independently of the contact sensor while operatively associated with the primary controller. While the Health Care Worker monitor may have displays or the like as shown in FIG. 12, they are not required.

The HCW monitor may also be co-operatively associated and co-located with a portable sanitizer to be worn by a health care worker. This combination (portable sanitizer/monitor) may be used in addition to or in lieu of the HCW monitor and fixed base sanitizer. Audible and visual annunciators are provided on both the primary controller and either monitor in order to provide information relating to the health care worker's hygiene status and/or proximity to the patient's intravenous catheter. Where practical, personal communication devices such as PDA's, pagers and badges may be considered as annunciators contained within the scope of this description.

A sanitizing device that may be employed in conjunction with the systems and methods described above is further provided. The sanitizing device is associated with a particular patient or a particular area of a health care facility and is capable of communicating with a controller. Employment of such a sanitizing device helps ensure that a health care worker has recently sanitized his or her hands or taken other appropriate sanitizing action prior to contacting a particular patient's intravenous catheter. The sanitizing device may be capable of receiving identification information from a monitor worn by a HCW via RF, IR, Ultrasound, digital imaging means (QR codes), a biometric device (Digital Facial Recognition) and/or a three-dimensional monitoring system that identifies the HCW using the sanitizing device. A portable sanitizing device is also provided that can perform the functions of a HCW monitor as well as being used for hand sanitation. The monitoring of hand washing compliance may be accomplished through means other than the sanitizing devices as disclosed. For example, a sensor may be incorporated as part of a sink and faucet assembly for determining whether a person has washed his hands. A successful hand washing may occur when the person has stood before a sink for a selected period of time, dispensed soap, and/or used a drying unit. Hand washing sensors and associated transmitters of compliance signals may also be included in hand sanitizer detections devices, devices such as automated alcohol or alcohol towelette dispensers, antiseptic dispensers, UV lights, glove dispensers or other monitored devices that may be used to sanitize hands.

A system for monitoring physical contact with or close proximity to a patient's intravenous catheter apparatus is provided. The system is capable of determining whether the Health Care Worker (HCW) making such contact or near contact is in compliance with institutional hygienic rules, and particularly hand washes rules. In one or more exemplary embodiments, it is further capable of determining whether a person who is contacting or manipulating a patient's intravenous catheter or its components presents a possible contamination threat irrespective of whether the person is wearing a monitoring device. One or more sensors are provided to detect the presence of person's hand on or near a patient's intravenous catheter assembly. The sensor(s) are preferably capable of communication with a processing unit comprised of a processor and an operational logic stored in a memory. To promote Health Care Worker compliance with institutional rules regarding hand sanitizing prior to contact with a patient's intravenous catheter apparatus, violators of such rules may receive audible and/or visual warnings while records are made of their identity, rule compliance and violations. The specification which follows provides exemplary and preferred embodiments. It should be understood that the invention is not intended to be limited to the particular embodiments disclosed herein, but on the contrary is intended to cover all modifications, equivalents and alternatives falling within the spirit and scope of the invention.

Figure 8:
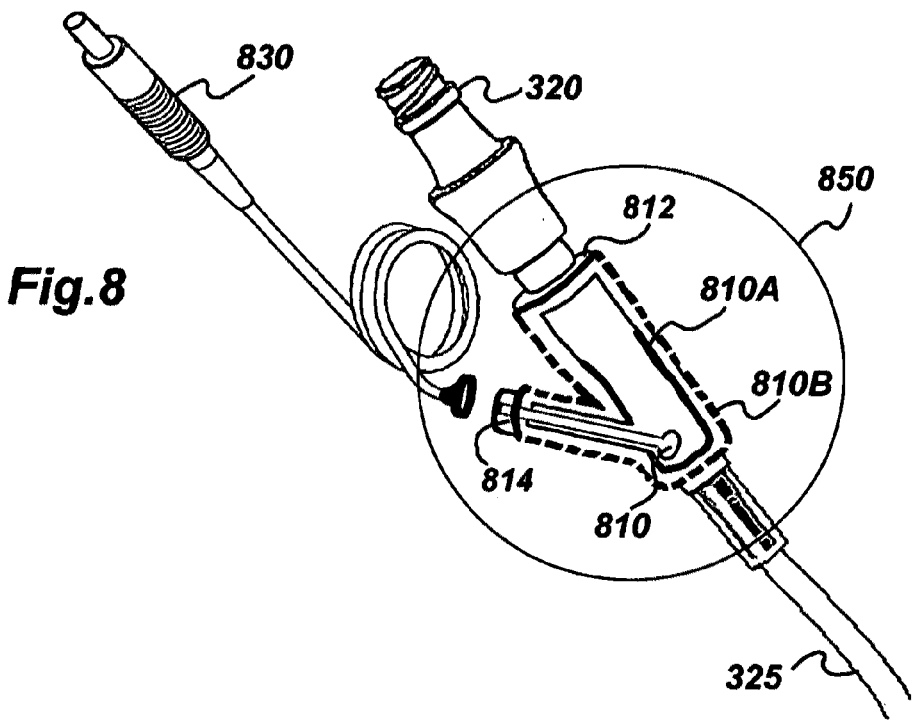
FIG. 8 is a diagrammatic illustration of a catheter assembly including a charge transfer sensor electrode usable with a catheter hygiene monitoring system.
Figure 18:
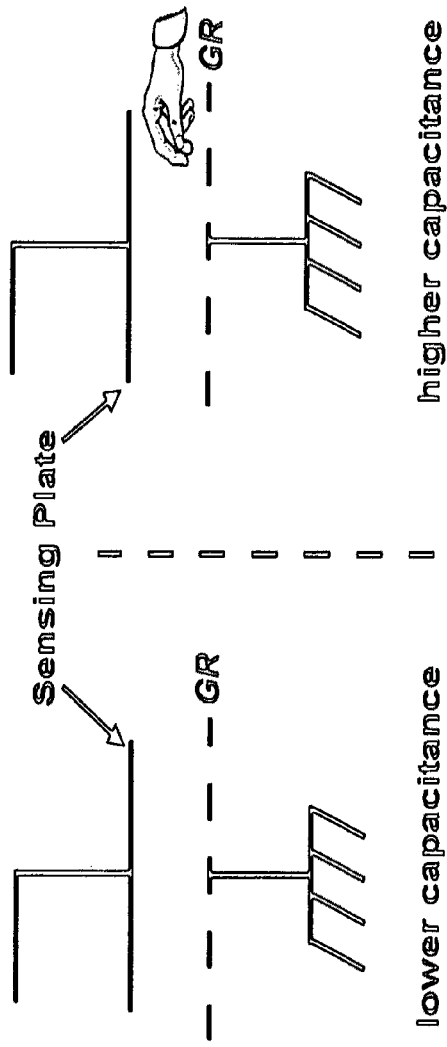
FIG. 18 is a diagrammatic illustration of a charge transfer detector usable with an intravenous catheter.
Figure 19:
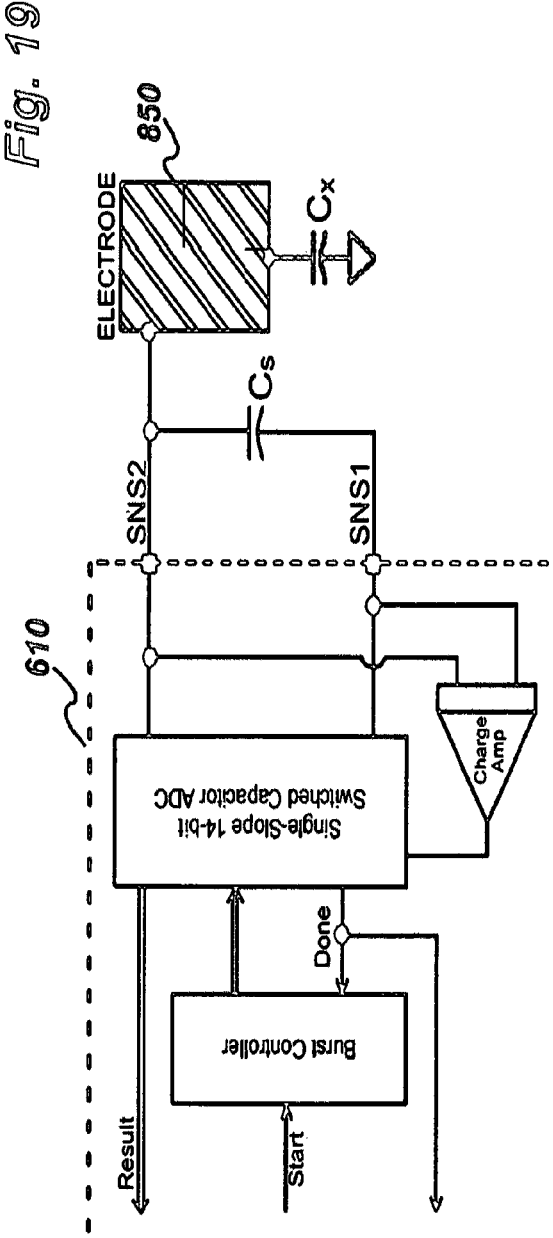
FIG. 19 is a schematic illustration of a charge transfer controller usable within a catheter hygiene monitoring system.
Figure 20:
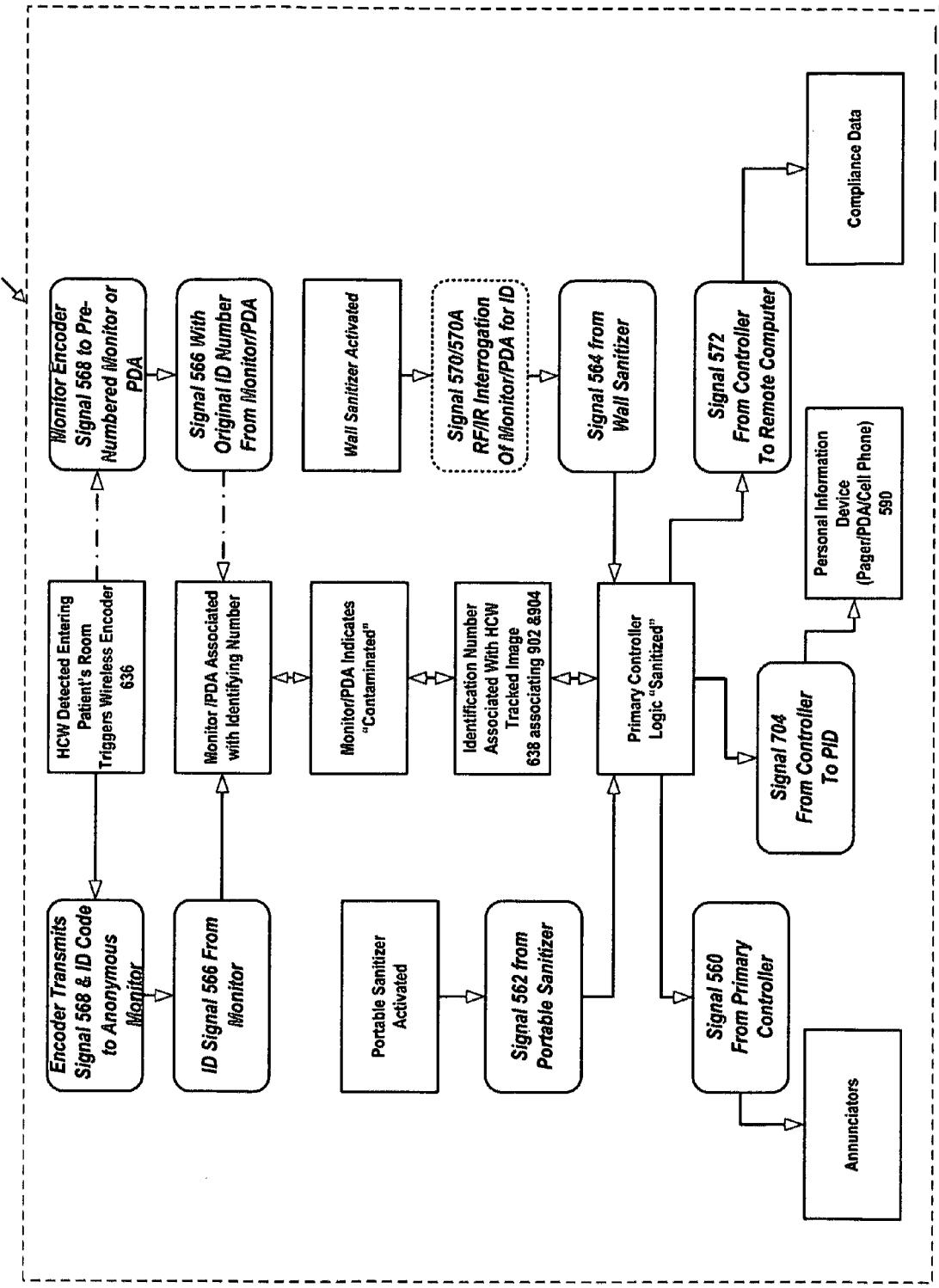
FIG. 20 is a flow diagram of the wireless signal paths interfacing the components of an operational hygiene monitoring system.
Figure 21:
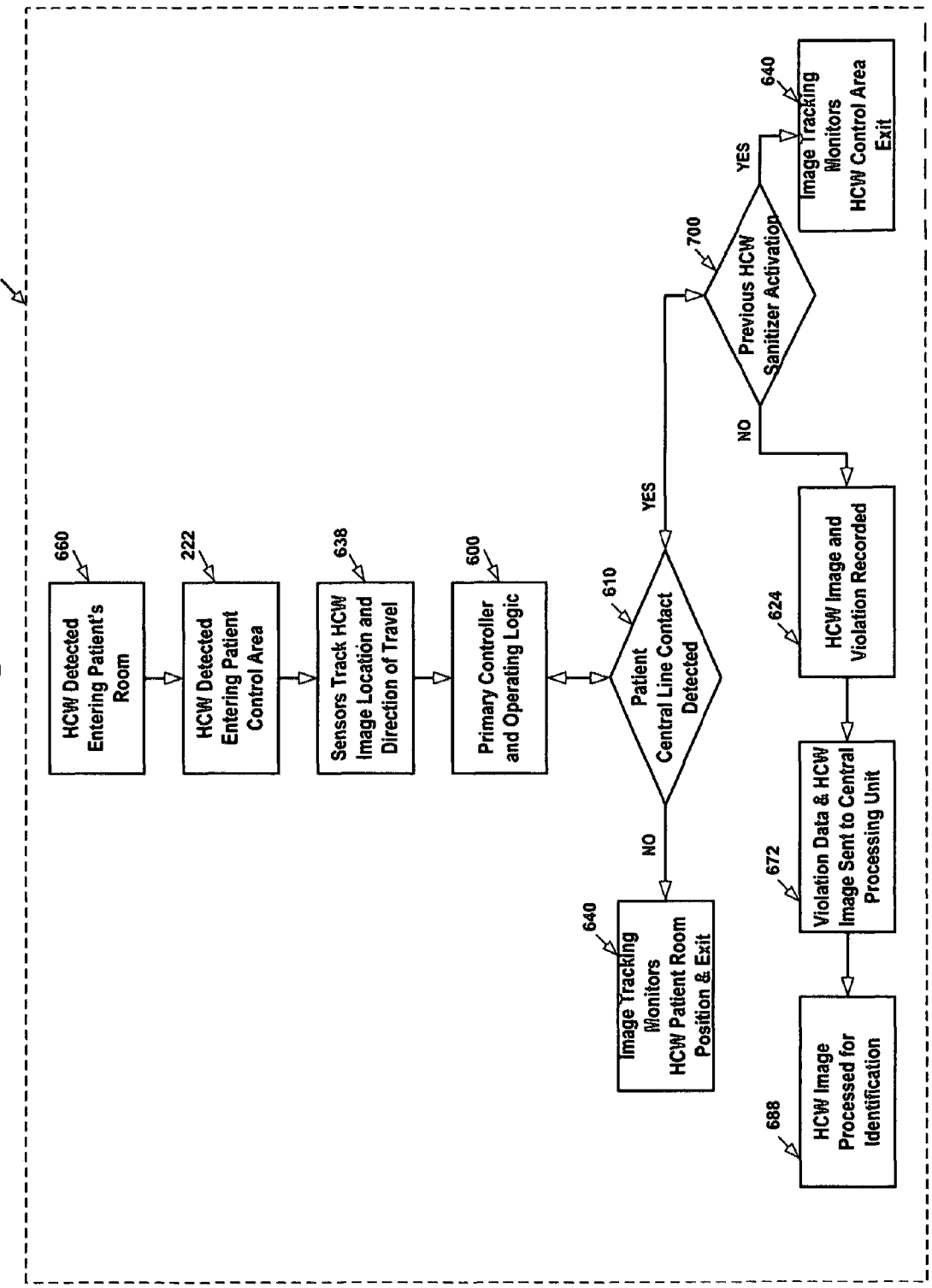
FIG. 21 is a flow diagram showing image tracking logic for tracking a health care worker.
Figure 22:
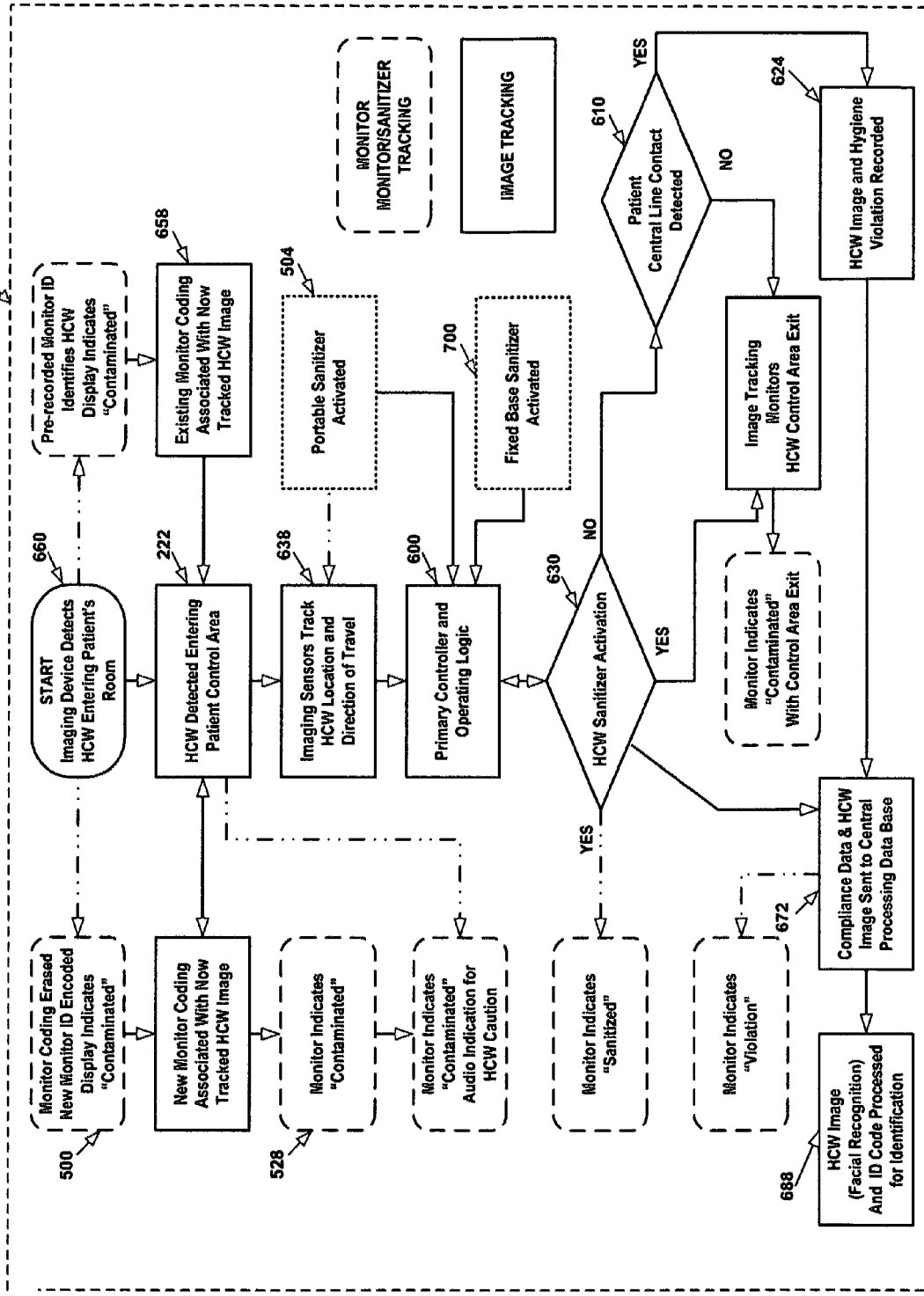
FIG. 22 is a flow diagram associating the monitor displays, sanitizer activation, image and/or monitor badge tracking logic and compliance data compilation in an operational catheter hygiene monitoring system.

Referring to FIGS. 18 and 19, charge transfer proximity detection can be described as follows. There exists a capacitance between any electrical surface reference point relative to ground, as long as electrical isolation exists between them. If this reference point is an intravenous catheter, then the positive plate of the capacitor is a sensing electrode 810 such as shown in FIG. 8, and the negative plate is formed by the surrounding area (virtual ground reference labeled GR in FIG. 18). When a hand is brought into close proximity (25 cm or less in this exemplary embodiment) of the sensing electrode, there will be increased coupling between the two and the capacitance of the detection electrode 810 and its electrically associated surface area, relative to ground will increase. Such capacitance is compared with a reference capacitor whose capacitance or charge may be altered so as to allow adjustment of the systems detection sensitivity. When the detection electrode is electrically associated with the fluids contained within an intravenous catheter, as described further below, a human hand will increase the capacitance between the sensing electrode and ground as a hand approaches a intravenous catheter that incorporates such a sensing electrode. Touching or close proximity to this electrode will increase the capacitance significantly as shown in FIG. 18. To measure a change in this capacitance, a preferred charge detection device may be similar to a charge transfer controller 610 as shown in FIG. 19. This device employs the charge transfer method of capacitive sensing. A charge is initially transferred to the all of the electrically contiguous parts of the intravenous catheter assembly 800 via electrical interconnect 830, thereby allowing it to function as a capacitor (CX) while a charge is transferred into a charge collection reference capacitor (CS) until the voltage on CS reaches a tripping point. FIG. 8 illustrates a detection electrode 810/810A consisting of an electrically conductive contact associated with the inside of the catheter lumen and/or fluid contained within housing 812 while an alternate configuration provides a detection electrode 810B which comprises an electrical association with an electrically conductive external surface of housing 812 in electrical contact with electrically conductive external surface of the catheter, which in either configuration of internal or external electrical contact, collectively or individually, is physically associated with housing 812 as an electrode assembly 850. This electrode assembly 850 provides an electrically conductive interface with the intravenous catheter fluid delivery tubing 325 and connectors 320 forming assembly 800. (All subsequent references to detection electrode 810/810A/810B and housing 812 will be referenced as electrode assembly 850). An electrical interconnect 830 is provided to electrically associate the electrode assemble 850 and any of the detection electrodes 810/810A/810B contained within, via optional electrical connector 814, with the charge transfer controller 610. The electrical interconnect 830, 814 and detection electrodes associated with the charge transfer sensor assembly may be incorporated along with contiguous intravenous catheter fluid conduction tubing 325 and Luer lock tubing connector 320 to form the intravenous catheter assembly 800 or alternately, electrode assembly 850 may be a discrete entity configured to be removably secured with or without electrical interconnect 830 to a co-operating intravenous catheter to form intravenous catheter assembly 800. Physical contact or near contact by a HCW with any of afore mentioned detection electrodes to possibly include IV fluid incorporated within the intravenous catheter assembly 800 causes charge transfer controller 610 to generate a signal 802 directed to the primary controller 600. Sensitivity control 662 is provided for setting hand and HCW proximity and contact detection thresholds for the primary controller 600. An electrical and fluid channel containing components collectively form a charge transfer proximity sensor assembly comprising an electrode within assembly 850 electrically coupled to a charge transfer controller circuit 610 operatively associated with the catheter assembly 800 via electrode assembly 850. The charge transfer proximity sensor assembly being configured to detect contact or close proximity by a person with the catheter assembly and generate an electrical signal responsive to such contact.

Erroneous indications of HCW hand contact with the patient's intravenous catheter assembly 800 which may appear from incidental contact with electrically conductive surfaces associated with the patient and medical apparatus surrounding the patient such as the patient's bed 922 or IV pole 316 may be avoided by the cooperative implementation of a driven shield 656 (see FIG. 14) that is electrically associated with the charge transfer controller 610. Stated simply, a signal equal in potential and frequency to the signal applied to the intravenous catheter assembly 800 is concurrently applied to those electrically conductive surfaces and medical devices surrounding the patient that are in near proximity and are not integral to assembly 800. An example of this application would be demonstrated by energizing IV pole 316 supporting the patient's intravenous catheter IV apparatus at the same frequency, pulse width and potential as the input to the electrode assembly 850. Similar in function to the principal of driving the shield of a RF energy carrying coax cable so as to avoid signal loss, this principal would serve to minimize a change in charge on electrically associated components of assembly 800 when contacting or near contacting the patient's IV pole or electrically conductive related medical equipment. Since both IV pole and sensor assembly would be placed in phase at the same electrical potential and charged and measured at the same frequency, no differential charge would exist between the two, thereby avoiding a charge transfer resulting in an erroneous indication of HCW contact or close proximity with the assembly 800. Alternately, the use of a multi-channel sensor instead of a single channel sensor and the use of a Boolean condition that must be true amongst two or more channels will provide logic to CPU 630 thereby avoiding a wrong trigger.

Figure 23:
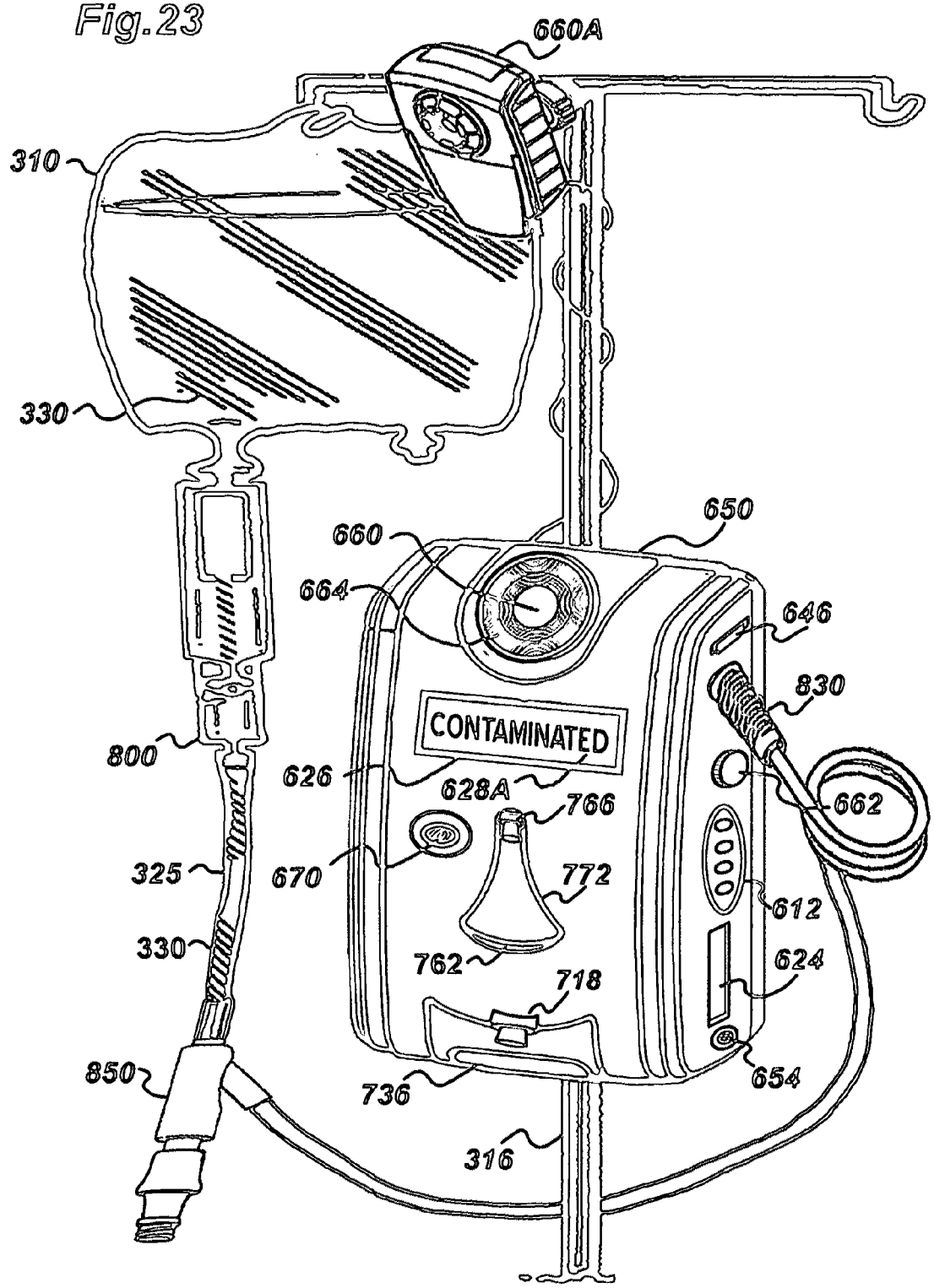
FIG. 23 is a diagrammatic view showing a intravenous catheter including a contact detector, a primary controller, an imaging device, an alcohol sensor and a sanitizer dispenser located on an IV pole as a single assembly.

Referring to FIG. 1 and FIG. 19, a patient's room is shown as equipped with a system 100 for monitoring compliance with institutional hand washing rules when contacting a patient's intravenous catheter assembly 800. As shown, a digital imaging sensor 660 and associated operating system routine 622 and image tracking routine 638 capable of position and motion direction detection is positioned to view the patient control area 210 that surrounds the patient. Object detection limiting software 640 associated with sensor 660's operating system ensures that it will not react to detection of ordinary movements of the patient while confined to a bed or chair (patient support apparatus) 260 within control area 210. A display device 426 is located just outside the room. A fixed base hand sanitizer 700 is shown on the wall within the patient's room, but additional or alternative sanitizers may be located within the patient's room. A patient 200 is shown within a patient control area 210, which is located within a patient's room 205. It will be appreciated that the room may contain more than one patients and more than one patient control area. The room includes an entrance, and the room area within the entrance may be considered a contaminated area 755 and is monitored by motion and digital imaging sensor 660. In the preferred embodiment one or more additional digital imaging sensors 660A is associated with digital imaging sensor 660 and may be positioned on opposing walls or ceiling to improve the field of view (FOV) associated with HCW detection and tracking and alternately provide 3-dimensional imaging of the patient control area 210 for enhanced HCW tracking when associated with the appropriate 3-D image processing software (not shown). A digital imaging sensor 660 shown in FIG. 1 or alternately a digital imaging sensor 660 located within integrated monitoring system 650 shown in FIG. 23 provides the ability to detect and monitor the identity of the HCW via a graphic QR code 578 present on their ID badge or system associated monitoring badge 558. Electro-optical detection and recognition of this code by digital imaging sensor 660 or QR ID Reading Sensor 670 and associated image processing firmware 640 (FIG. 14) provides CPU 630 with HCW identity information to be integrated with subsequent HCW hygiene actions and protocol compliance. Remote display device 426 is located just outside the room to provide notification of hygiene violations to administrators. A hand sanitizer 700 is shown within the patient's room near the patient. The fixed base hand sanitizer 700 includes a dispensing sensor 718 operatively associated with a transceiver 792 capable of generating an activation signal 564. It further includes an annunciator 726, which may be in the form of an LCD display or a speaker 788 associated with a pre-recorded audio announcement 734 directing proper hand sanitizing procedures. The hand sanitizer 700 shown is a "bag-in-box" type dispenser that receives a bladder filled with soap or other sanitizing agent.

In the preferred embodiment, the patient's room 205 is equipped with a system consisting of one or more digital imaging devices. The digital imaging sensor (s) 660 in conjunction with an operating routine 622 within EEPROM 648 and associated CPU 630 acting as position sensor(s) in conjunction with image processing 640 and image tracking 638 is employed in the patient's room to, in conjunction with one or more fixed base or portable sanitizers, determine the hygiene status and proximity of a health care worker 222 to the patient's intravenous catheter assembly 800 in one or more increments of increasing or decreasing proximity. Continuous monitoring of persons near the patient is provided by the system 100 via tracked HCW image 902 irrespective of whether the persons who may come into contact with the patient's intravenous catheter assembly 800, are wearing monitors or not. Such monitoring maybe accomplished with minimal power requirements and extended battery life as the entire system can effectively be in a "sleep mode" until detection, by an optional PIR motion detector or proximity sensor 661, of an HCW's entry into the patient's room 205 prior to entry into patient control area 210.

The digital imaging sensor 660 and an associated operating system may be capable of recognizing the HCW as a unique human entity and may also be incorporated in such a manner as to observe the HCW's physical location and direction of travel within the patient's room and their increasing or decreasing proximity to the patient's intravenous catheter and the patient's associated fixed base sanitizer. Coincidence of the digital image 902 of the HCW's near proximity (preferably <2 meters) to the patient's associated fixed base sanitizer 700 concurrent with operation of said sanitizer as determined by activation of dispensing actuator 718 and the generation of a signal 564 in cooperation with the primary controller 600, may be used to indicate that the specifically tracked HCW, and image of such operator of the sanitizer 902, is then associated with a sanitized logic state (logic "1") e.g. HCW image may associated with a system generated green box image. Subsequent to the HCW sanitizing their hands, the digital imaging sensor 660 and associated operating system will continue to differentiate that HCW and their tracked image 902 as being sanitized while continuing to observe all other sanitized and non-sanitized persons e.g. person images contained within a system generated red box within the patient control area 210. In addition to or in lieu of, personal identification information 904 derived from interrogation of HCW monitor 500 or recognition of HCW's QR code 578 when entering patient's room, other identifying information of the HCW may be associated with tracked image 902 by near field interrogation of the HCW proper via biometrics or via encoder decoder 636 interrogation of HCW's monitor or ID badge when entering patient's room or when located in near proximity to the sanitizer during sanitizer activation. Such interrogation to include but not limited to digital image scanning of HCW's biometrics, RF/IR interrogation of ID monitor or quick response code (QR code) on HCW's ID badge, captured during a sanitizing operation of the fixed base sanitizer.

One exemplary embodiment utilizes electronic imaging to monitor the use of a sanitizer by a HCW, thereby determining the hygiene status while concurrently tracking and determining the HCW's proximity to the patient. The utilization of image processing firmware 640 capable of obscuring or distorting the tracked image 904 of the HCW and patient 200 is preferably employed so as to render the identity of the patient and HCW tracked images unrecognizable as to conform to HIPA requirements for maintaining patient confidentiality unless forensic analysis of a hygiene or safety protocol violation is required. Such analysis, to include recording images of the violation and events preceding the violation (forensic documentation) that may include images of the violator if positive identification of the HCW via their monitor is not possible, may be accomplished at the patient's primary controller location or the data may be subsequently forwarded by wired or wireless means 672 to a remote computer location 688 for hygiene compliance data collection, recordation and optionally, ID analysis to include facial recognition image processing for identification of the monitored HCW. Various commercially available protocols may be utilized for generation of a spreadsheet reflecting analysis of the hygiene protocol compliance data collected by system 100. A number of alternate means may be employed for the determination of HCW's identity and their proximity to the patient. These methods include serialized RFID badges, RFID proximity sensors, IR code detection and identification, biometric (to include facial recognition) detection, Zigbee, RFID or IR zone detection means may, for example, be employed to detect when a person is standing near the patient and determine the identity and hygiene status of said person.

An exemplary embodiment utilizes digital imaging and tracking via digital imaging sensor(s) 660, thereby providing a robust means by which the system 100 is able to distinguish HCW proximity to the patient with a finer degree of distance resolution and repeatability than those methods mentioned supra. Digital imaging, when programmed to do so, provides a reliable means of tracking both monitored and non-monitor wearing HCW's or visitor's while determining and documenting their activation of a particular fixed base sanitizer as well as determining with fine resolution complex geometric detection areas, their proximity in decreasing and increasing increments of distance to a patient and the patient's intravenous catheter assembly 800.

The preferred method of determining a HCW's contact or near contact with a patient's intravenous catheter assembly is through the use of a charge transfer proximity sensor including one or more electrically conductive electrodes 810/810A or 810B contained on or within a preferably plastic but optionally metallic or electrically conductive housing 812 comprising electrode assembly 850 incorporated within or functionally associated with the intravenous catheter assembly 800 and electrically associated via electrical interconnect 830 with a charge transfer controller circuit 610 capable of detecting a charge transfer indicating contact or near contact of a person's hand with an electrode or IV fluid electrically associated with the patient's catheter assembly 800. Upon a change in charge on the electrode assembly 850 and/or its associated catheter, containing liquids or fluids 330 (these terms to be used interchangeably) within the fluid channels of electrode assembly 850, tubing 325 and connectors 320, caused by hand contact or close proximity of a hand, the electrode assembly 850 is capable of sending signals via electrical interconnect 830 to charge transfer controller 610 operatively associated with primary controller's CPU 630 contained within primary controller 600. The preferable charge transfer contact sensor configuration is placement of a non-corrosive detection electrode 810 configured as a probe or alternately, detection electrode 810A configured as an electrically conductive coating, in electrical contact with the IV fluids encountered when intravenous catheter assembly 800 is performing its designed function of providing fluids to a patient. These fluids are typically isotonic ionic (0.9% saline) and therefore are electrically conductive in nature. When in contact with the fluids, due to electrical conductivity, either electrode enables the electrically conductive fluid stream to become an integral part of the charge transfer contact detection circuit thereby allowing the entire length of the fluid stream to function as an electrode. Another iteration provides a means whereby catheter assembly 800 described above and electrode assembly 850 is associated with an external electrically conductive coating or shell on the housing assembly 812 comprising detection electrode 810B which is associated with a intravenous catheter assembly incorporating an electrically conductive exterior coating or wire conductor thereby forming a continual electrical circuit running either partly or the entire length of the intravenous catheter This configuration is designed to have a hand contact detection range preferably limited to not more than 25 centimeters and preferably less than 5 centimeters from almost any point on the length of the contained fluid stream or tubing length so as to avoid the possibly introduction of contamination into same while providing a reasonable certainty that a HCW is touching or almost touching the central venous catheter assembly 800 and its associated plumbing before being detected and hygiene status indicated. This range limitation allows the system to operate effectively while avoiding erroneous triggering by the patient or patient interactions with nearby objects thereby generating false notifications.

Alternatively, to be used in lieu of, or in combination with, the previously mentioned central venous catheter assembly configuration a charge transfer contact sensor may be configured in such a manner that all or part of the tubing and associated connectors, ports and adapters of the intravenous catheter assembly 800 are electrically conductive on the internal or external surface of the tubing and electrode assembly 850, irrespective of the fluid contained within, either through material composition, embedded wiring or electrically conductive coating 810B shown in FIG. 8. As such, electrical contact with the charge transfer electrode may be established via a conductive clamp or other means to allow a continuous electrical path encompassing all or part of the length of the central venous catheter assembly electrically associated with electrical interconnect 830 thereby making at least part of the entire apparatus a charge transfer electrode.

Figure 13:
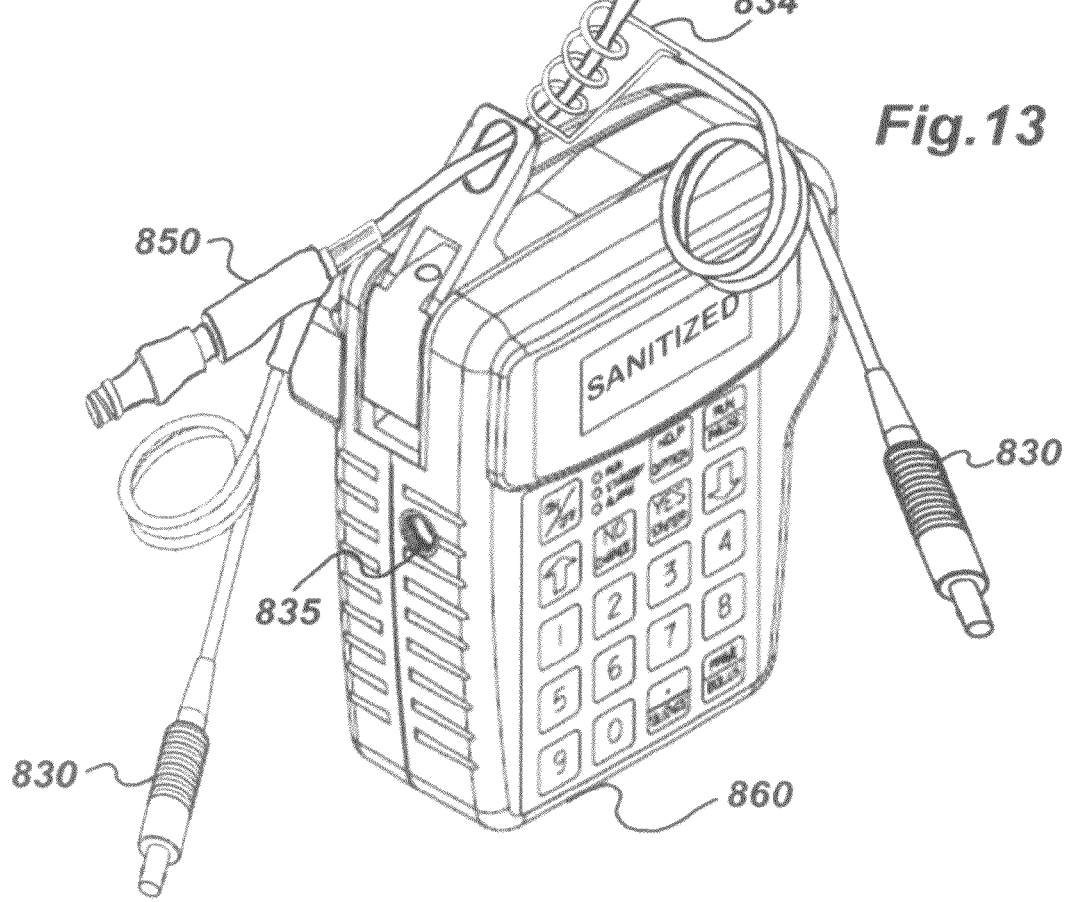
FIG. 13 is a diagrammatic illustration of a conductive and an inductive contact detector sensor electrode operatively associated with an automated infusion pump.
Figure 26:
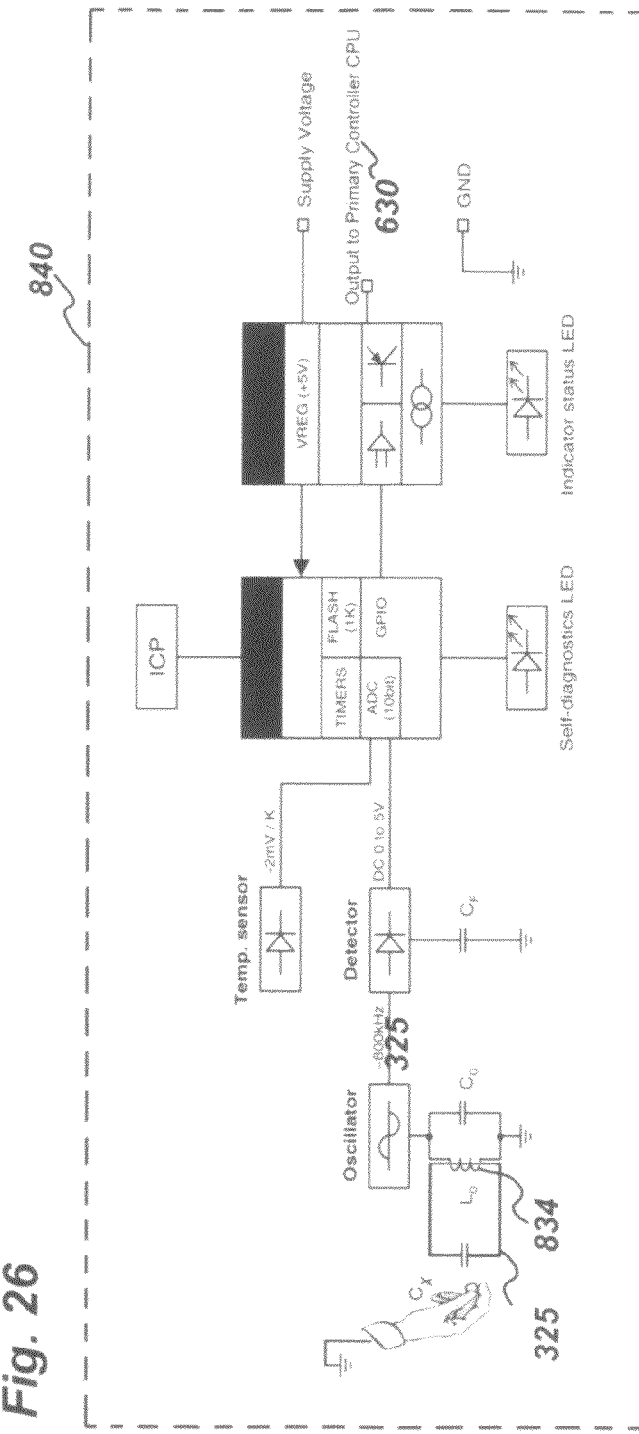
FIG. 26 is a schematic view of the inductively coupled contact controller.
Figure 27:
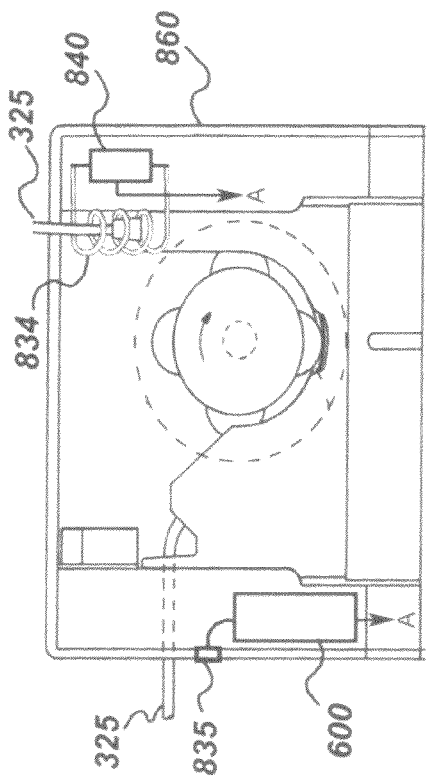
FIG. 27 is a perspective view of an inductively and conductively coupled intravenous catheter contact detection system operative associated and contained in the housing of a metered intravenous catheter associated infusion pump.

A third exemplary iteration of an electrical interface between all or part of a central venous catheter assembly 800 as a charge transfer sensor and an inductive charge transfer controller 840 operatively associated with a coupled induction coil 834 shown in FIGS. 13, 26 and 27. A single length or one or more loops of a fluid filled or conductive intravenous catheter may run through the center of an induction coil 834 associated with an oscillator via the connector 830 which is operatively associated with a charge transfer sensor circuit. Contact or near contact with the intravenous catheter assembly 800 will cause a change in electrical characteristics of the tuned circuit associated with the coil 834 thereby changing its oscillating frequency which when coupled to a frequency to voltage converter, A/D converter or other device sensitive to a frequency change thereby generating a signal indicating aforementioned contact or near contact of a hand with the patient's intravenous catheter assembly 800. The sensors controller may consist of a HF oscillator circuit based on the Colpitts oscillator type which has a simple circuit configuration which produces a clean sinusoidal wave signal and is capable of oscillating in a wide frequency range. A resonant circuit consisting of inductor L1 834 and capacitor $C_O$ determines the frequency of these oscillations. Introduction of additional capacitance $C_x$ through hand contact with the patient's catheter assembly 800 (capacitance $C_y$) which is electrically associated with tank circuit $L1/C_O$ will cause a change in the oscillator frequency resulting in a change in logic output, as illustrated in FIG. 26.

FIG. 27 illustrates the implementation of an inductive coupling 834 of a intravenous catheter 800 to a primary controller 600 via an inductively or capacitively reactive contact controller 840 associated with a contact and monitoring detection system 100 assembled in a metered intravenous catheter automatic infusion pump. Similarly illustrated in FIG. 13, is the implementation of an inductively or conductively coupled catheter tubing 325 containing IV fluid 330 associated with an infusion pump.

In FIG. 1 a patient 200 is shown attached to a monitored intravenous catheter assembly 800, all of which are located within a patient care area 210. It will be appreciated that the room may contain more than one patient and more than one patient care area. The room includes an entrance within the patients room 205. The entrance may be considered a contaminated area 755. The hospital room is equipped with a system of Health Care Worker (HCW) motion and tracking sensors. These sensors are preferably though not necessarily digital imaging sensor (s) 660 associated with detection 640 and tracking 638 operating routine designed to track and determine the presence and proximity of a health care worker 222 to the patient 200 in one or more increments of increasing or decreasing proximity. Alternate means of determining HCW presence and location may be employed as detectors in the room e.g. passive infrared (PIR) detectors (not shown). In the preferred embodiment, a PIR motion detector sensor 661 selectively sensitive to the entry and exit of anyone entering the patients room is provided so as to allow the HealthCare Worker's position and digital imaging 660 be designed to have image processing firmware 666 mediated field of view capabilities, thus requiring a person to be initially outside the patient care area 210 before being actively detected entering this area so as to cause image tracking to be initiated (unless behavioral studies require additional room entry data). This configuration of sensors provides a means of energy management and robustness e.g. requiring someone other than the patient to be detected by the PIR detector 661 entering the patient's room prior to the activation of the monitoring and tracking system as well as minimizing erroneous intravenous catheter contact indications by the fact that HCW entry into patient's room 205 must be detected prior to the primary controller indicating a hygiene violation. As shown in FIG. 1, digital imaging sensor 660 and associated image processing routine 640 capable of position and motion detection is positioned to view the patient control area 210. Active area detection software associated with imaging sensor 660 image processing system 666 provides a means of specifying and limiting areas of image detection so as to ensure no detection or recording of the patient's recognizable image while patient is confined to a bed or chair (patient support apparatus) within the control area 210 unless specifically programmed to do so. An annunciator display device 426 is located just outside the room. A hand sanitizer 700 is shown on the wall within the patient's room, but additional or alternative sanitizers or sanitizer detectors may be located within the patient's room. Optionally, a table or support surface for assembly 340 is provided for storage and/or assembly of the intravenous catheter assembly 800 and is operatively associated with monitoring system 100. Contact with this table or support surface 340 as determined by aforementioned charge transfer detection without proper hand hygiene as determined by hygiene system 100 may elicit a similar response as seen with contact with a patient's intravenous catheter assembly 800, thereby causing the indication and recordation of a hand hygiene contact violation if not properly sanitized.

Figure 2:
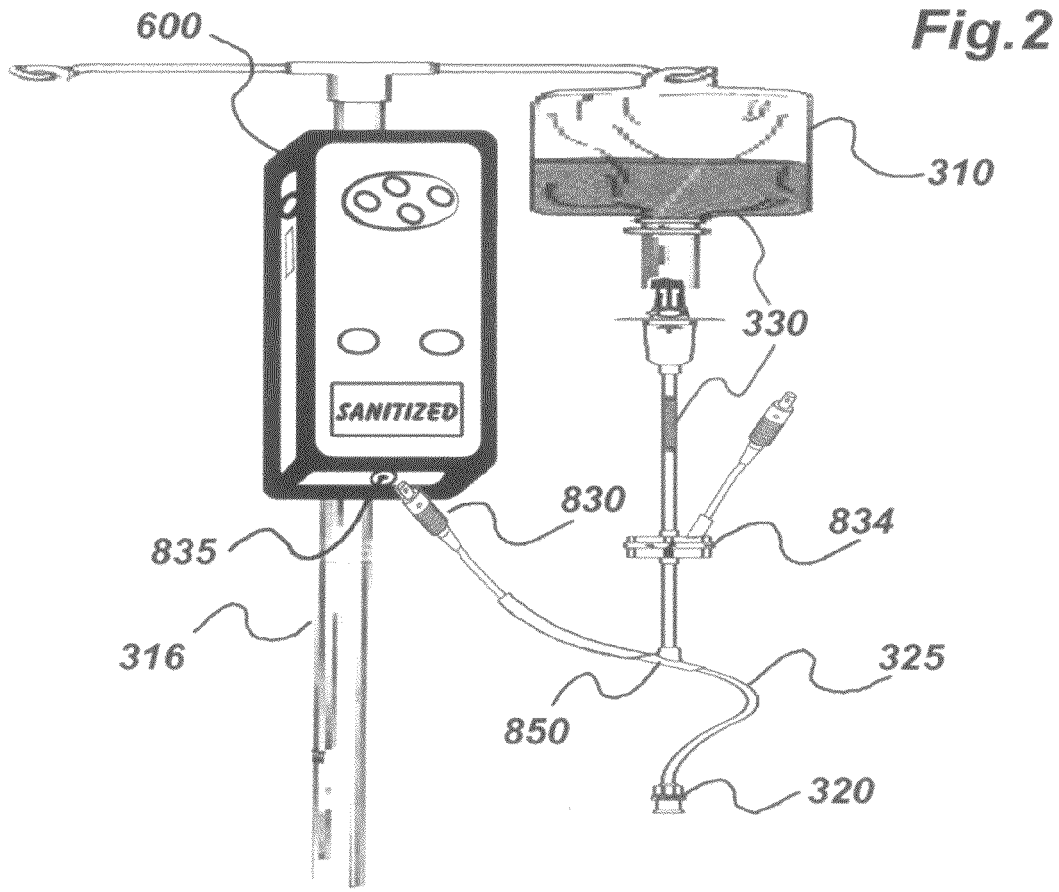
FIG. 2 is a perspective view showing, IV bag, supporting pole and a patient's intravenous catheter operatively associated with a catheter hygiene monitoring system.
Figure 3:
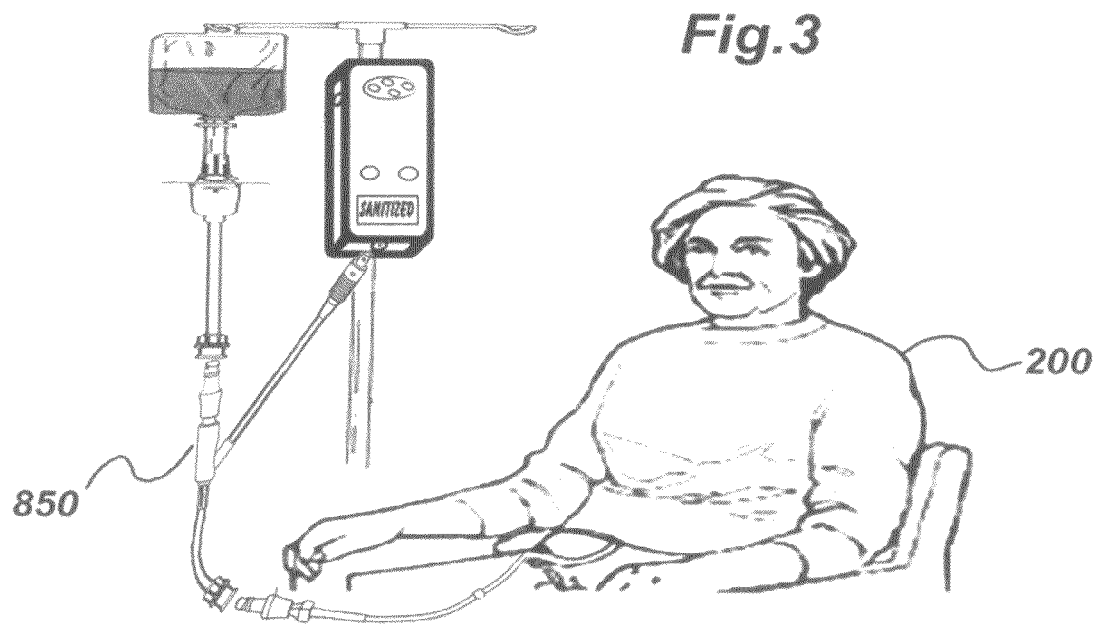
FIG. 3 is a perspective view of a catheter hygiene monitoring system and central venous catheter associated with a patient.
Figure 6:
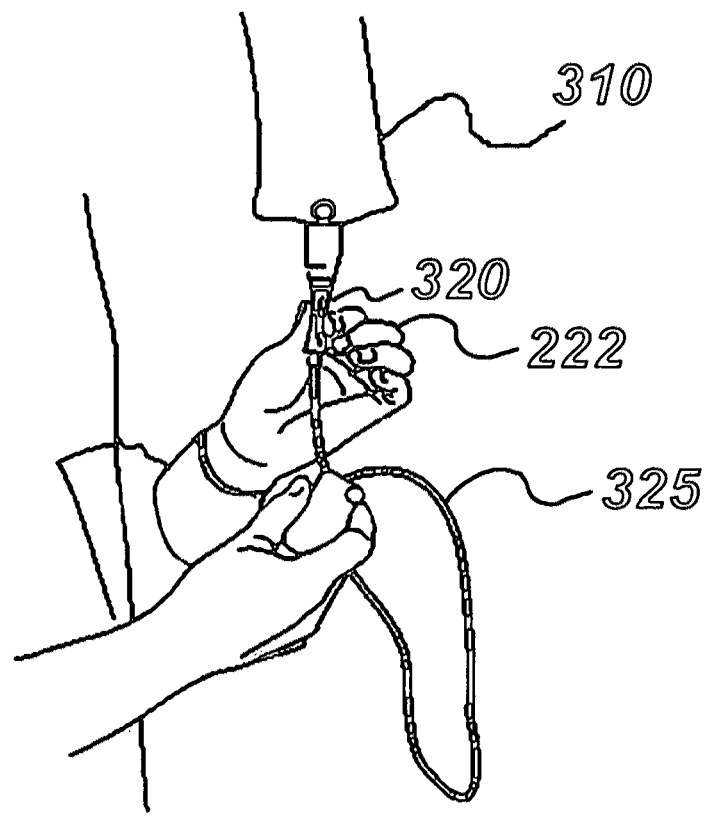
FIG. 6 is a perspective view demonstrating potential contamination of an intravenous catheter while being inserted into an IV bag by a health care worker.
Figure 7:
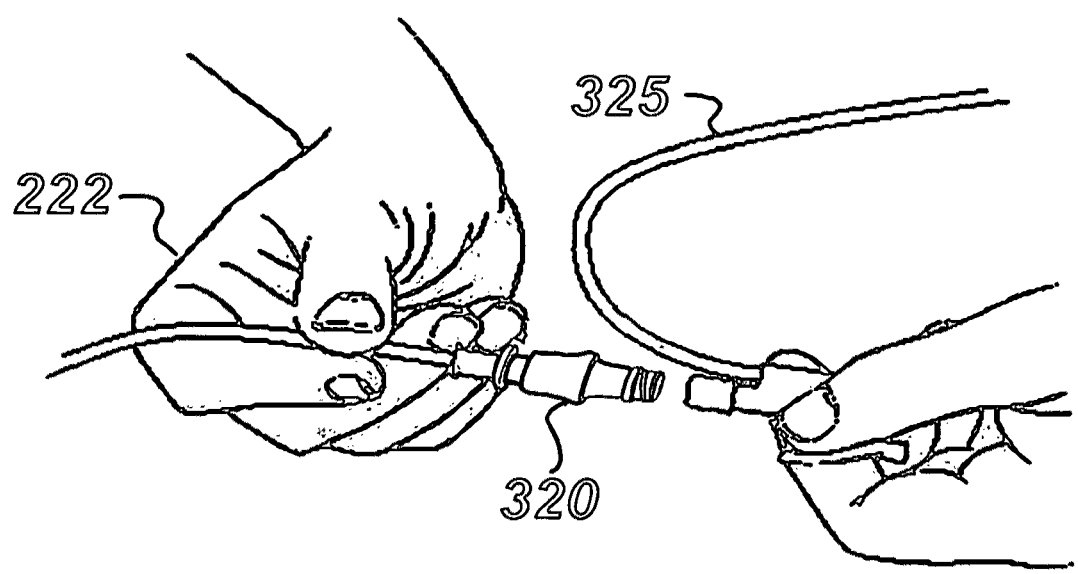
FIG. 7 is a perspective view of potential contamination of an intravenous catheter when being manipulated during assembly by a health care worker.

The HCW's imaging sensor(s) 660 are preferably located and/or directed near where the patient in a patient support device 260 will likely be located while a person standing near the patient will also be detected. Software associated with the digital imaging 660 that is capable of isolating and obscuring the patient's image so as to make the patient identity unrecognizable within the viewed scene (FOV) is provided 666, while still maintaining positional information of the patient and the HCW, thereby allowing detection and tracking 638 of the HCW/visitor as a distinct and separate entity from the patient. The preferred use of multiple detection zones allows the system 100 to distinguish between degrees of proximity of the HCW to a patient and direction of travel of the HCW (to or from the patient) if programmed to do so. Digital imaging sensor 660 may alternatively provide redundancy, ensuring that a health care worker will indeed be detected by at least one of the detectors. In the preferred embodiment, the specificity of range and direction detection by digital imaging allows the system to operate effectively in rooms having multiple patient care areas without interfering with health care workers who do not enter a specific patient's care area 210 or contact the patient's intravenous catheter assembly 800. It will be appreciated that the use of RFID badge detection, IR Zone detectors and Zig-Bee mesh networks as an alternate means of locating and monitoring direction of movement of the HCW is anticipated within the monitoring system 100. While potentially functional in this capacity, RFID technology by design lacks specificity of geometric and special resolution and as the patient control area 210 (especially patient control areas in multi-patient rooms) to be monitored are of such geometric shape and proximity as to preclude precise and reliably accurate detection and tracking via radio detection means. IR zone detectors suffer from a similar lack of specificity with resultant lack of dimensional and proximity resolution. Different position and motion sensors may have different ranges as deemed appropriate. Referring to FIG. 2, a patient's IV pole 316 equipped with an intravenous solution bag 310 is shown as equipped with a primary controller 600 and associated electrode assembly 850 as part of intravenous catheter assembly 800 cooperating with system 100 for monitoring compliance with institutional hand washing rules when contacting a patient's intravenous catheter.

FIG. 5A schematically illustrates a very basic but functional intravenous catheter contact monitoring system in accordance with an exemplary embodiment. FIG. 5B schematically illustrates the system components of a preferable intravenous catheter monitoring system 100. FIGS. 11 and 23 show a QR ID Reading Sensor 670.

Figure 14:
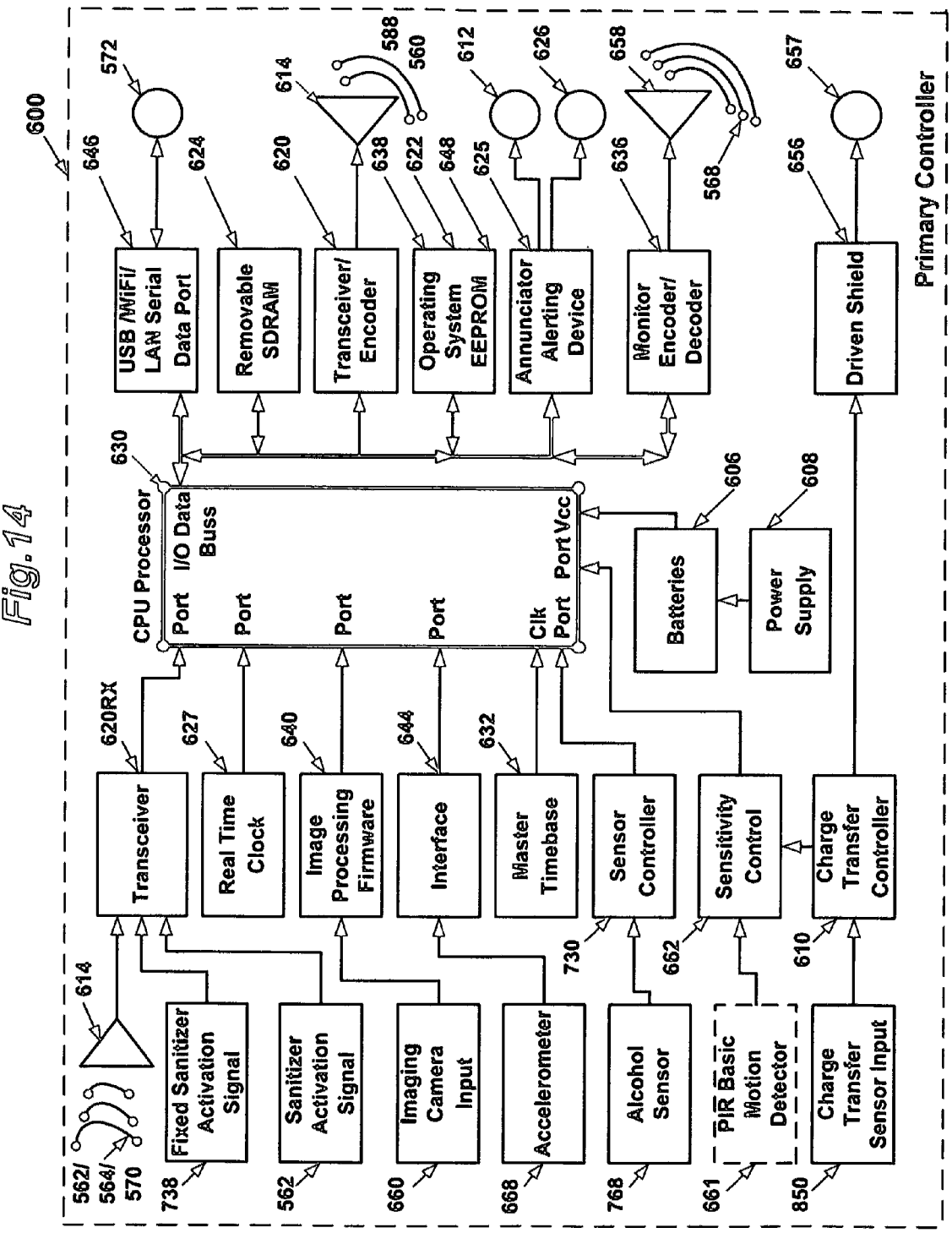
FIG. 14 is a schematic illustration of a primary controller and charge transfer sensor as shown in FIG. 10.

FIG. 5B shows a means of compliance data acquisition to include a violation recorder and processor FIGS. 10 and 14 show the primary controller 600 in further detail. Shown are, motion sensor 668, electrode assembly 850, digital imaging sensor(s) 660, image and ID code processor 640, a fixed base sanitizer 700, a portable sanitizer/monitor 500, an alcohol sanitizer sensor 768, radio transceiver 620, annunciator 625 and the manner in which they communicate and interfacing with primary controller 600.

The primary controller includes a power source such as batteries 606, a power supply 608. Notification of a low battery condition is preferably conveyed by means of an indicator, such as the LCD display 626 that is included with the controller. The primary controller 600 includes a CPU Processor 630 configured to receive information or instructions from integrated and remote hardware and to cause the operation of other integral or remote devices. A CPU 630 is provided that is capable of communicating with one or more of the annunciators 426,526, 626 and 726 preferably via a transceiver/encoder. While shown as a separate unit, the primary controller 600 may be incorporated within the sanitizer 700 along with HCW proximity detector 660 as shown in FIG. 23. The patient care area digital imaging sensor 660 is wired or wirelessly coupled to the primary controller CPU 630 through image processing firmware 640. A first memory such as an EEPROM 648 and operating system 622, and a second, preferably removable memory 624 are operatively associated with the CPU. A removable, non-volatile memory such as an SDRAM 624 stores certain information that must be retained if the power source is interrupted, to include but not limited to information relating to the patient and cause the display of such information on one or more of the provided annunciators, Stored data may include pertinent patient data such as the patient's name, drug allergies, special care needs and/or other patient-specific information, any or all of which can be displayed on annunciator 626, the time and nature of hygiene protocol compliance and violations, including video observations of hand washing rule violations, HCW identity, station location and patient ID information. A power switch 654 is provided for activating and inactivating the system. Transceiver 620 RX/TX associated with antenna 614 is incorporated in the primary controller 600 and provides a means for wirelessly transmitting signals 560 and optionally 568 to and receiving signals 566, 562 and 564 from sanitizer 700, monitor 510 and sanitizer/monitor 500. A serial bus/USB connector and associated serial data port 646 allows for programming the primary controller and allowing operational and compliance/violation information to be uploaded and downloaded 672 to a remote computer and memory 688.

Figure 9:
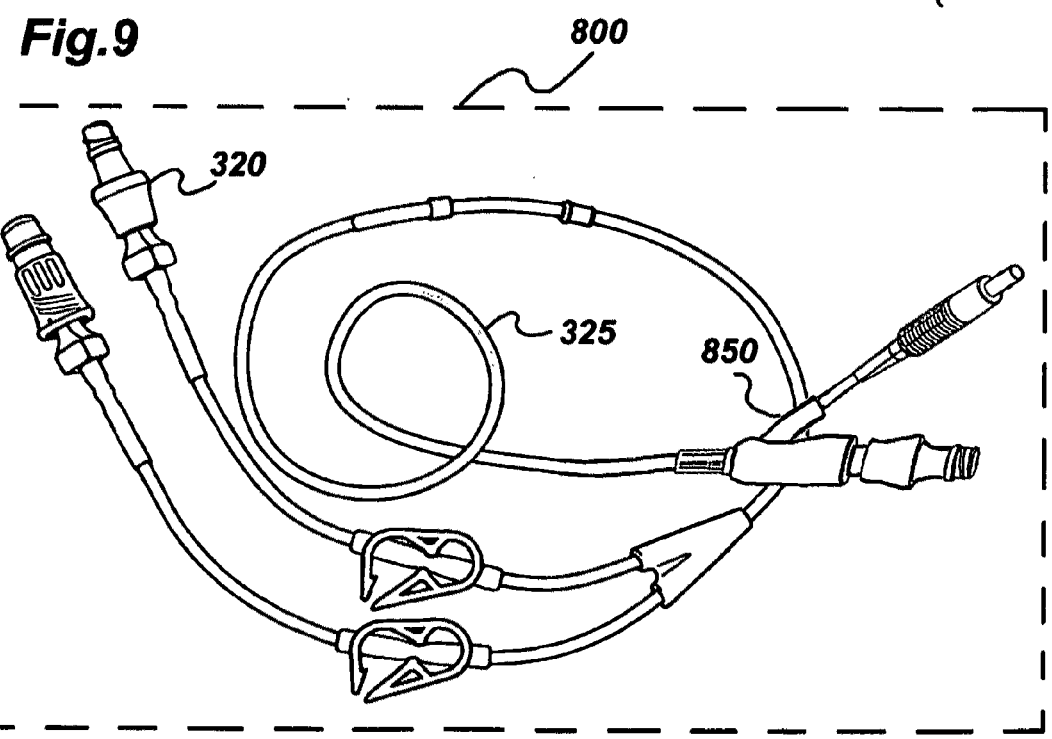
FIG. 9 is a diagrammatic illustration of a multi-feed intravenous catheter assembly including a charge transfer sensor electrode.

A CPU 630 is employed for executing stored instructions. An operating system 622 is incorporated into an EEPROM memory 648 that stores instructions which can be retrieved and executed by the CPU 630. Charge transfer contact sensor electrode 810 and the patient care area 210 motion and tracking processing routine 638 and imaging sensor 660, as described above, communicate with the primary controller via an interface 644. Such communication can be wireless or with the use of wires. The master time base 632 provides machine cycles for the primary controller CPU 630 and watchdog timers (not shown) which monitors, when required, time between HCW hand sanitizing actions and contact with patient's intravenous catheter. A real time clock 627 provides time stamp information to the CPU for documenting timing of health care worker compliance actions and/or violations. The transport of fluids associated with the patient's central venous catheter is facilitated by means familiar to those of skill in the art, such as a fluid-containing IV bag 310. One or more removable securable fluid interconnections, typically of luer-lock configuration 320 and/or additional tubing 325 is provided so as to communicate with additional associated tubing or interconnect devices comprising the associated fluid path. It will be appreciated that various types of connectors, tubes, clamps and other elements may be included in the intravenous line assembly 800, such as those shown in FIG. 9.

The primary controller 600 is shown in greater detail in FIG. 10. This assembly of components provides the central processing for the hygiene monitoring system 100. It is capable of sending signals and receiving signals from all the associated sub systems of hygiene monitoring system 100. The primary controller incorporates a CPU 630 in conjunction with operating system 622 so as to determine the functioning of these components. Included in the primary controller is a charge transfer controller 610. Upon detection of change in charge in its associated electrode 810 this controller generates a signal 802. The primary controller 600 is capable of causing the generation and transmission of encoding signal 568 by wireless encoder 636 to HCW monitor 510 and HCW sanitizer/monitor 500. In response to this radio interrogation, monitors 500 and 510 will either respond with their pre-encoded identifying signal 566 or allow themselves to be encoded with a unique identifying code thereby generating a handshake using such communication protocol but not limited to Blue Tooth/Wi-Fi/LAN between the monitor and HCW monitor or sanitizer/monitor. A real time clock 627 is provided for displaying time and noting the time of HCW entry into control zone 210, time of sanitizing actions, time between sanitizing action and intravenous catheter contact and time stamping hygiene compliance and possible hygiene protocol violations. Annunciators 426, 526, 626, 726 and 914 similar to those described above, allow visual and/or audio messages to be provided. In addition to these displays, various alternatives are contemplated for alerting the health care worker in the event it is determined that the worker is not in compliance with the institution's hand washing protocol. Alternately, a radio signal, with such communication protocol but not limited to Blue Tooth/Wi-Fi/LAN 704 may be generated by the primary controller's transceiver 620 to elicit an alert on the attending HCW's cell phone or pager in a manner to cause the individuals PID 590 (personal information device) to function as an annunciator and alert them as to their hygiene status. Other elements of the primary controller are found in FIG. 14 and do not require further description. It will be appreciated that some redundancy is built into the elements of the system described herein, which is preferred but is not considered essential. All detectors and proximity sensors employed in the system may be sensor assemblies including integrated circuits providing noise filtration and/or sensitivity adjustments.

Activation of the primary controller is preferably dependent on initial detection of the entry of a HCW/visitor into a patient's room 205. Initial HCW detection may be accomplished via digital imaging associated with image tracking 638 digital imaging sensors 660 or by a PIR motion detector 661. In one or more exemplary embodiments, the requirement of first detection of HCW entry into patient control area 210 to activate the intravenous catheter contact monitoring process, provides a means of minimizing the probability of a patient initiated "intravenous catheter contact" indication, as an immobile patient typically would not be associated with a intravenous catheter contact contamination and concurrently be some distance from their intravenous catheter assembly 800. To address such possible occurrences that may arise from an ambulatory patient attached to a intravenous catheter, the primary controller may incorporate an accelerometer 668 ("G" sensor) that is responsive to movement of the primary controller or IV line itself. If the patient and their associated primary controller are ambulatory and moving e.g. attached to the patient's moving IV pole 316 then the primary controller's associated logic and detection function may be automatically suspended. FIGS. 5A and 5B schematically illustrates the basic components of the monitoring system inclusive of the primary controller and the manner in which they communicate with each other. Other features of the primary controller 600 may include a call switch (not shown) to allow the patient to send a signal to a nursing station or elsewhere and a patient accessible reset switch (not shown) if an erroneous intravenous catheter contact violation indication should occur.

Figure 28:
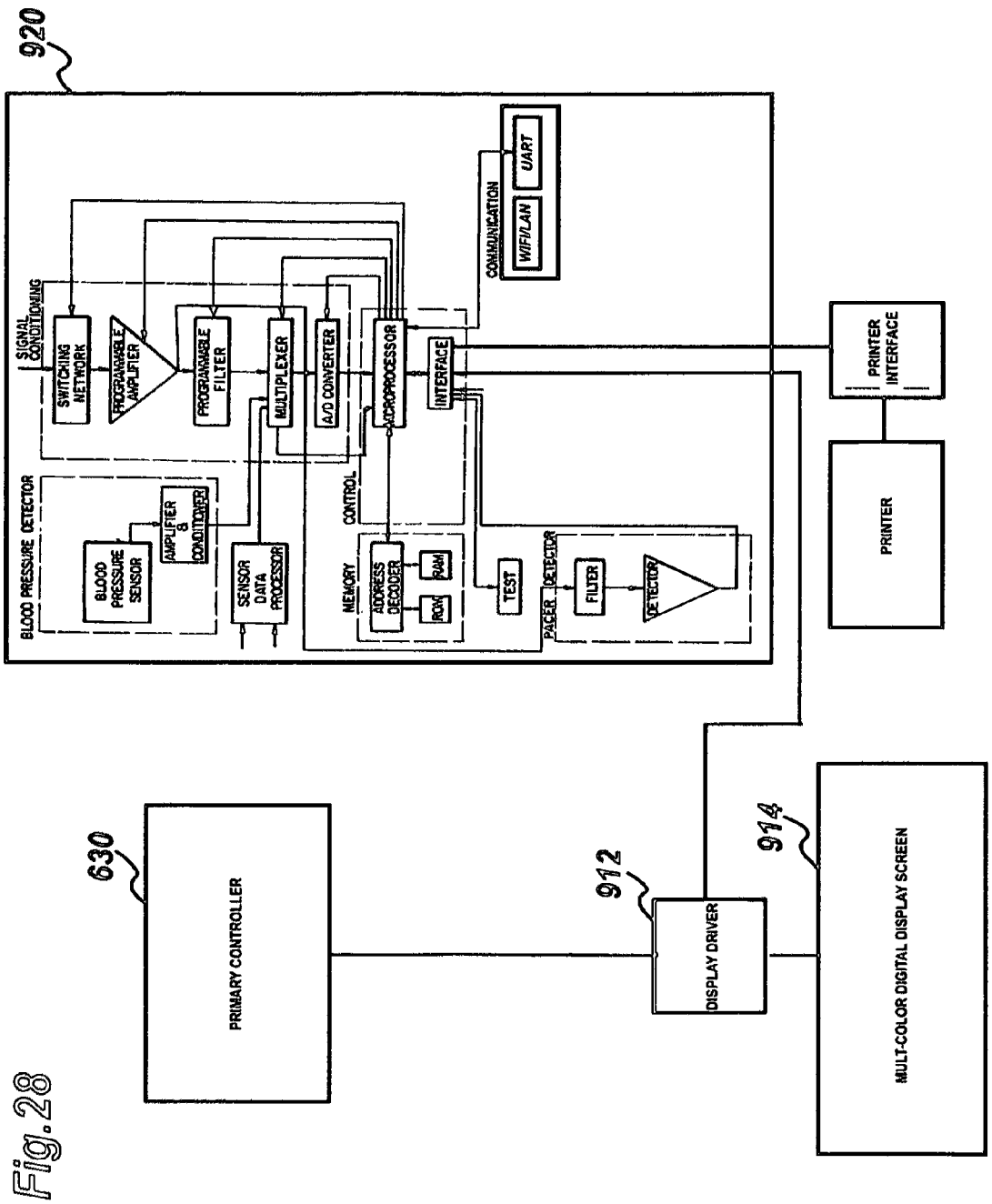
FIG. 28 is a schematic illustration of a patient centric graphic display co-operatively shared between a hygiene monitoring system and a physiologic monitoring system.

FIG. 28 illustrates how the primary controller may further include the ability to communicate wired or wirelessly with a physiologic monitoring system 920 present in the patient's room. Space for instrumentation is limited in a patient's room and visibility of pertinent information is paramount. An HCW viewing a patient's physiologic parameters, in all probability would be in near contact with the patient and/or their intravenous catheter and prove to be a contamination risk unless properly sanitized. The capability of prominently placing and co-locating both physiologic information from a device functioning as an ECG, BP, pulse-oximeter or similar monitoring system and hand hygiene status information as determined by hygiene monitoring system 100 associated with primary controller 630 on the same monitor display screen 914 controlled by a display screen driver 912, optimizes the use and functionality of both systems. Alternately, information relating to operation of an infusion pump 860 or auto syringe or an alternate physiological monitoring device, (not shown) may be operatively associated, integrated and/or co-located with the primary controller 600 or integrated intravenous catheter monitoring system 650 so as to create a system of hybrid functionality.

Figure 15:
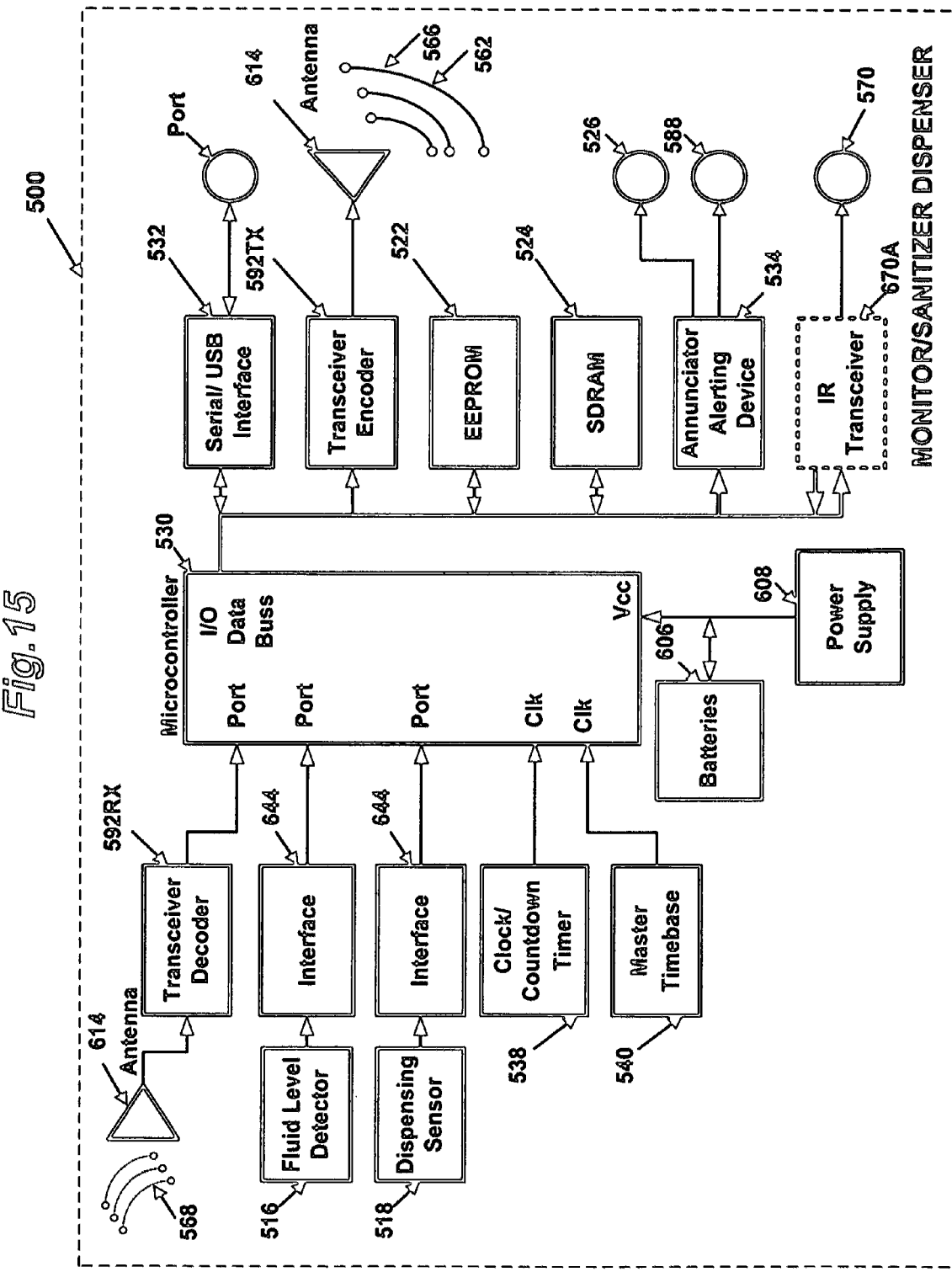
FIG. 15 is a schematic illustration of a portable monitor operatively associated with a portable sanitizer dispenser assembly as shown in FIGS. 16A and 16B.

FIGS. 12 and 15 illustrate monitor 500. This HCW monitor can be affixed to a chain or cord (not shown) and worn around the neck and/or include a clip 558 for fastening it to the HCW or visitor's clothing. The HCW/visitor monitor 500 includes a number of elements common to the primary controller and the sanitizer/monitor assembly 510, including a central processing unit 530, a memory including an operating system, an LCD display 526, an LED display 584, a transceiver 592 for receiving a signal 568 and transmitting a 566 to and from the primary controller 600. The visitor monitor (not shown) may have the same capabilities as the HCW monitor and be programmable in the same manner, but would not necessarily include specific information such as picture and related quick response identification code (QR) 578 relating to the identity of the visitor. The monitor's annunciator 526 maybe remotely activated and a hygiene message 628A,B,C displayed when the primary controller associated with either PIR 661 and/or motion and tracking routine 638 and sensor 660 has determined a health care worker 222 entering or exiting the patient's room 205 and control area 210. Detection of HCW 222 entry in to the patient's room 205 by motion detector 661 causes the primary controller 600 to generate low power directional signal 568 to be transmitted to the monitor 500 by monitor encoder 636 via monitor encoder antenna 658 thereby causing the status of the monitor annunciator 526 to display a "contaminated" message 628A. Detection of the HCW image 902 in very near proximity to sanitizer 700 by motion and tracking sensor 660 cooperating with image tracking routine 638 and the concurrent detection of actuation of the associated sanitizing device actuator 718 within patient control area 210 may cause a directional, low power near field signal 560 to be generated by the primary controller transceiver 620 causing the monitor's annunciator to display a "Hands Sanitized" message" 628B, illuminate or change color of indicator LED 584 and/or cause an audible indication on audio annunciator 588 while concurrently associating the tracked HCW's image 902 and ID code 904 with a logic "1" indicating a sanitized status. When the worker or visitor leaves control area 210 (the area surrounding the patient) and/or exits the patient's room 205 as determined by tracking the location of HCW image 902, the primary controller may cause, via wireless means, the HCW monitor's annunciator to display a "Sanitize When Leaving" message 628C. Many elements comprising the HCW monitor 500 are common to those of other monitors and controllers discussed above, and some of the same reference numerals are accordingly employed to designate them. The monitor is intended to operate independently of the contact sensor controller 610 while operatively associated with the primary controller 600. While the monitor may have displays or the like as shown in FIG. 12, they are not required.

An alternative embodiment of the wall sanitizer 700 is provided. A monitor operatively associated with a sanitizer is shown in FIGS. 16A/B and 15, thus providing further details of the sanitizer/monitor 510 combination intended to be carried by health care workers. This hand sanitizer 500 may be used in place of or in addition to the fixed base hand sanitizer 700 described below. The sanitizer/monitor 500 is designed for portability, and could perform the functions of the HCW monitor 510 and the wall-mounted sanitizer 700, thereby obviating the need for both. It could be designed to fit in a pocket or affixed to a belt or other article of clothing. Unlike the sanitizer 700 described below, the portable sanitizer/monitor 500 would not be associated with a particular room or patient. A pump-type dispenser 504 is shown in the drawings, though other mechanisms for dispensing sanitizing material can alternatively be employed. The sanitizer includes a sensor 518 to detect when sanitizing material has been dispensed. This sensor could, for example, detect a change in pressure in the container portion of the sanitizer when the pump is actuated. Other features of the portable sanitizer disclosed herein include a fluid level detector 516. Activation of the sanitizer dispenser switch 518 by the HCW causes the generation of a signal 562 via wireless communication through transceiver 592 indicating sanitizer activation to include an identifying code associated with that particular monitor/sanitizer. The sanitizer is preferably employed in near proximity to the patient 200 such that its operation is in near proximity to the patient's intravenous catheter assembly 800 thereby minimizing possible opportunities for subsequent contamination of HCW's hands prior to contact with the intravenous catheter. The sanitizer's location at the time of activation, being determined by tracking routine 638 and imaging sensor 660 monitoring location of HCW image 902 associated with that particular monitor ID code 904. Similar in function to the wall-mounted sanitizer 700 as discussed above, it is preferably activated subsequent to detection of the health care worker's entry into patient control area 210. Detection of a signal 562 when initiated in an appropriate area as determined by the primary controller may cause a "sanitized" message to be generated on the monitor display 526 or speaker 588 of monitor/sanitizer 500 and/or monitor 510, an announcement could be similarly displayed on annunciator 626 associated with the primary controller 600. Preferably, detection of a signal 562 not generated in the patient control area as determined by the primary controller's image tracking of the associated HCW will not result in the generation of a logic "1" indicating a sanitized state as determined by the primary controller. Associated annunciators will continue to indicate a previously encoded "contaminated" condition.

As shown in FIGS. 15, 16 and 16A, the sanitizer/monitor 500 may include various means of communicating warnings, such as an LCD annunciator display 526, a speaker 588 and/or a vibration mechanism 536. A countdown timer 538 and audio circuit 534 are incorporated to provide guidance via annunciators 526 and 588 regarding the appropriate period for hand rubbing subsequent to application of sanitizer to the hands. The warning mechanisms are preferably designed to avoid disturbing a sleeping or resting patient while providing adequate prompting to the health care worker to sanitize their hands. The system 100 including the portable sanitizer/monitor 500 and one or more location tracking routines 638 and sensors 660 associated with primary controller 600 tracking HCW image 902 preferably ensures that the health care worker will be in a patient care area 210 in near proximity to the patient when requested to sanitize his/her hands by an annunciator 526/588/626/914. Alternately, the hygiene monitoring system 100 may further provide the health care worker with the option of not using the sanitizer 700 or sanitizer/monitor 510 while still remaining within the institutional hand washing rules if the immediate actions that are to be taken by the health care worker do not involve contact with the patient's intravenous catheter assembly 800. For example, if the health care worker is simply viewing the patients intravenous line or alternately a medical apparatus associated with the patient and does not cause the activation of the intravenous catheter contact controller 610 via contact with intravenous catheter assembly 800 associated with the patient, then preferably, a caution announcement may be generated relative to their detection in patient control area 210 on physiologic monitor multi-color graphic display screen 914. An additional example, if the health care worker does not cause activation of the position or proximity sensor system 600/638 or optionally 601 associated with the patient control area 210, no warning is generated and a violation of the rules would not be recorded. If contact with the patient's intravenous catheter is not made and sanitizing material has not been dispensed by fixed base sanitizer 700 or portable sanitizer/monitor 500 within a predefined period within patient control area no violation of hygiene protocol will be noted. This will preclude any action on the part of the primary controller that would cause the indication or recordation of a violation. If, however, the health care worker has not so actuated the sanitizers within the required time and/or distance from the patient, as noted by the absence of generated activation signals 562 or 564, upon receipt of a contact signal associated with contact controller 610 determining contact with intravenous catheter assembly 800, the primary controller will cause an imaging and identification record of a violation to be made by digital imaging device 660 to include time and location and generate a warning signal or message to be generated or displayed on its associated annunciators. The transmission of signal 562 or 564 to primary controller 600 associated with the activation of sanitizer 700 or sanitizer/monitor 500 by HCW will cause the generation of a sanitized logic "1" associated with tracked image 902 within controller 600 and a "hands sanitized acknowledgement" graphic animation (not shown) to appear on graphic display screen 914 or a "hands sanitized" message 628B to appear on annunciators 526, 626 and 726 in response to signal 560 from primary controller 600 reflecting same. HCW contact with the patient's intravenous catheter assembly 800 within patient control area 210 subsequent to the monitored dispensing of sanitizer within a predefined period of time and distance from the patient's intravenous catheter, will preclude any action on the part of the primary controller that would cause the indication or recordation of a violation regardless of subsequent activation of the intravenous catheter contact sensor 810 by that specific HCW prior to that specific HCW exiting patient control area 210.

As mentioned above, the portable sanitizer/monitor 500 may be programmed to perform the functions of the HCW monitor badge 510. Such sanitizer/monitor may be pre-programmed with an identification code directly associated with a specific HCW. Alternately, it may be configured to be responsive to a programming signal 568 containing a discrete identification code 904 from the wireless monitor encoder 636 via associated directional antenna 658 in cooperation with primary controller 600 such that it would cause annunciator 526/626 and 726 to indicate a "contaminated message" 628A upon HCW entering the patient's room. Such signal is generated and transmitted in response to detection of HCW's entry into the patient's room by preferably by motion detector 661 or alternately, digital imaging sensor(s) 600 in cooperation with motion and tracking firmware routine 638 associated with CPU 630. The tracked image of the HCW 902 within tracking routine 638 is thereby associated with a discrete identification code 904 now associated with the aforementioned HCW monitor or sanitizer/monitor. Alternately, the HCW's monitor or sanitizer/monitor may, in response to reception of signal 568, transmit a pre-programmed identity code previously associated with said HCW and their sanitizer/monitor, back to the primary controller 600 via wireless monitor encoder/decoder 636 or controller transceiver 620 via antenna 614 to then be associated with the HCW's now tracked image 902. While the electronic communication process is preferably accomplished via wireless radio means, IR data transmissions utilizing IR transceivers may be utilized to accomplish similar results. Preferably, the HCW associated portable sanitizer/monitor 500 is actuated after the HCW or visitor is detected entering patient room 205 and subsequently detected and tracked in patient control area 210 by digital imaging device(s) 600 and image tracking routine 638. Such actuation transmits an identification code, 904 either indigenous or previously encoded by encoder 636 indicative of HCW activation of the hand sanitizer. Upon detection of portable sanitizer/monitor activation by the HCW with ID number 904 in the appropriate location 210 as determined by image tracking of HCW image 902 associated with ID number 904 as determined by operating routine 640, the image coding and status of the HCW is changed to "sanitized" logic "1" and an appropriate signal 560 is sent by the primary controller 600 to the monitor or sanitizer/monitor causing annunciator 526/626 and 726 to indicate "sanitized" message 628B. Alternately, upon receipt of encoded signal 568 the monitor transceiver 592 may transmit a pre-programmed identifier code and signal 566 associated with that particular monitor badge and/or associated with the identity of the monitor's HCW or visitor bearing said monitor to the primary controller's transceiver 620. Receipt of sanitizer activation signal 562 by monitor 510 will cause annunciator 526 operatively associated with monitor microprocessor 530 to display a "sanitized" message 628B.

Contact with the patient's intravenous catheter assembly 800 by such a sanitized logic "1" HCW will result in no announcement or may result in an annunciator indicating proper protocol compliance. Such compliance may also be recorded directly or remotely via signal 572 for record compilation. In the preferred embodiment, actuation of the sanitizer/monitor outside of the patient control area 210 as determined by tracking routine 638 monitoring tracked HCW image 902 and may be considered as non-responsive by the controller system 600 and may be interpreted as if the HCW has not sanitized their hands at all, thereby resulting in their hygiene status remaining as a "contaminated" logic "0", along with message 628A and a violation will be noted by primary controller 600 if and when HCW contact or the close proximity of HCW's hand with/to the patient's intravenous catheter assembly 800 is determined by hygiene monitoring system 100. Concurrently, if activation of an associated sanitizer is not indicated upon detection of the departure of the HCW from patient control area 210 when HCW contact or proximity with intravenous catheter assembly 800 has been determined, a violation of hygiene protocol may be recorded if hygiene protocol requires HCW sanitizing when leaving a patient.

Figure 17:
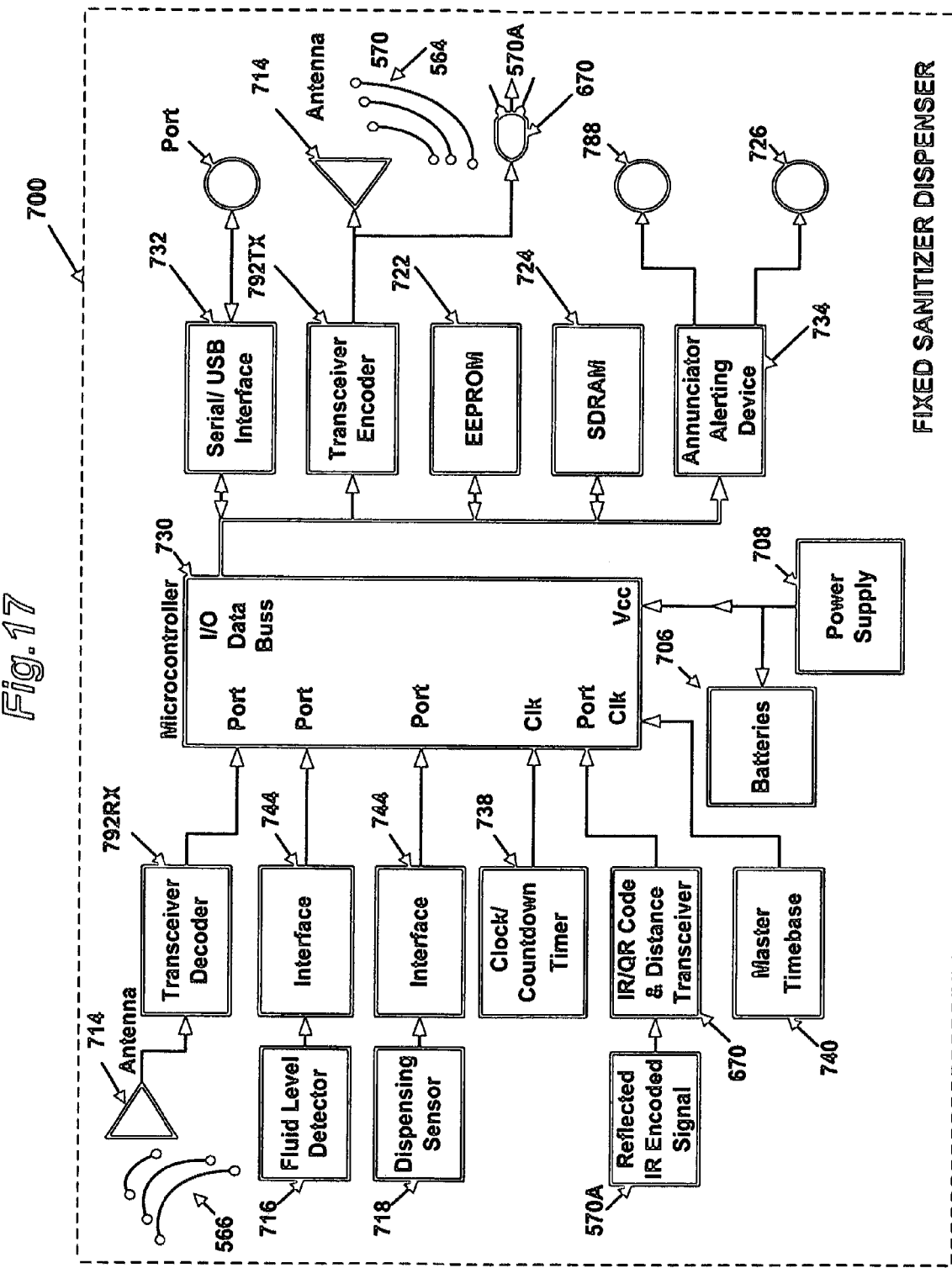
FIG. 17 is a schematic illustration of a fixed base sanitizer usable with the hygiene monitoring system shown in FIG. 11.

FIGS. 11 and 17 provide a schematic and perspective view of the fixed base hand sanitizer 700 employed in the system shown in FIG. 1. It includes a sensor 718 that, when actuated, will cause the dispensing of sanitizer while concurrently transmitting and activation signal 564. Additionally, fixed base sanitizer transceiver 792 and antenna 714 enables the sanitizer to receive encoded signals from the primary controller transceiver 620 that will cause sanitizer microcontroller 730 to acknowledge receipt of such transmission (handshake) and generate a sanitized message 628B on associated display 726. Receipt of either of these encoded discrete identification numbers 904 by primary controller CPU 630 will result in electronically associating one or both of these identity numbers with the electronically tracked image 902 of the HCW who is currently within a small defined space operatively associated and contiguous to the fixed base sanitizer being activated.

Activation of the fixed base sanitizer dispenser 700 by the HCW will cause a message 628B to be generated on the associated annunciators reflecting completion of hand sanitizing procedures. The sanitizer is preferably programmed and located such that it is associated with a particular patient, a patient care area 210, and/or a patient's room. It includes an annunciator 726, which may be in the form of an LCD display and a speaker 788. The speaker is associated with an audio driver 734 and an audio program so as to provide prompting to the HCW to rub their hands together for a finite period of time after application of the hand sanitizer as per hygiene protocol. The sanitizer 700 further includes a transceiver 792 with an associated antenna 714. Upon activation and dispensing of sanitizer by the fixed base sanitizer, the antenna associated with the sanitizers transceiver 792 transmits an encoded compliance signal 564 that is received by the primary controller transceiver 620 and concurrently the monitor badge's transceiver 510 via its associated antenna 614 and transceiver 592.

Figure 25:
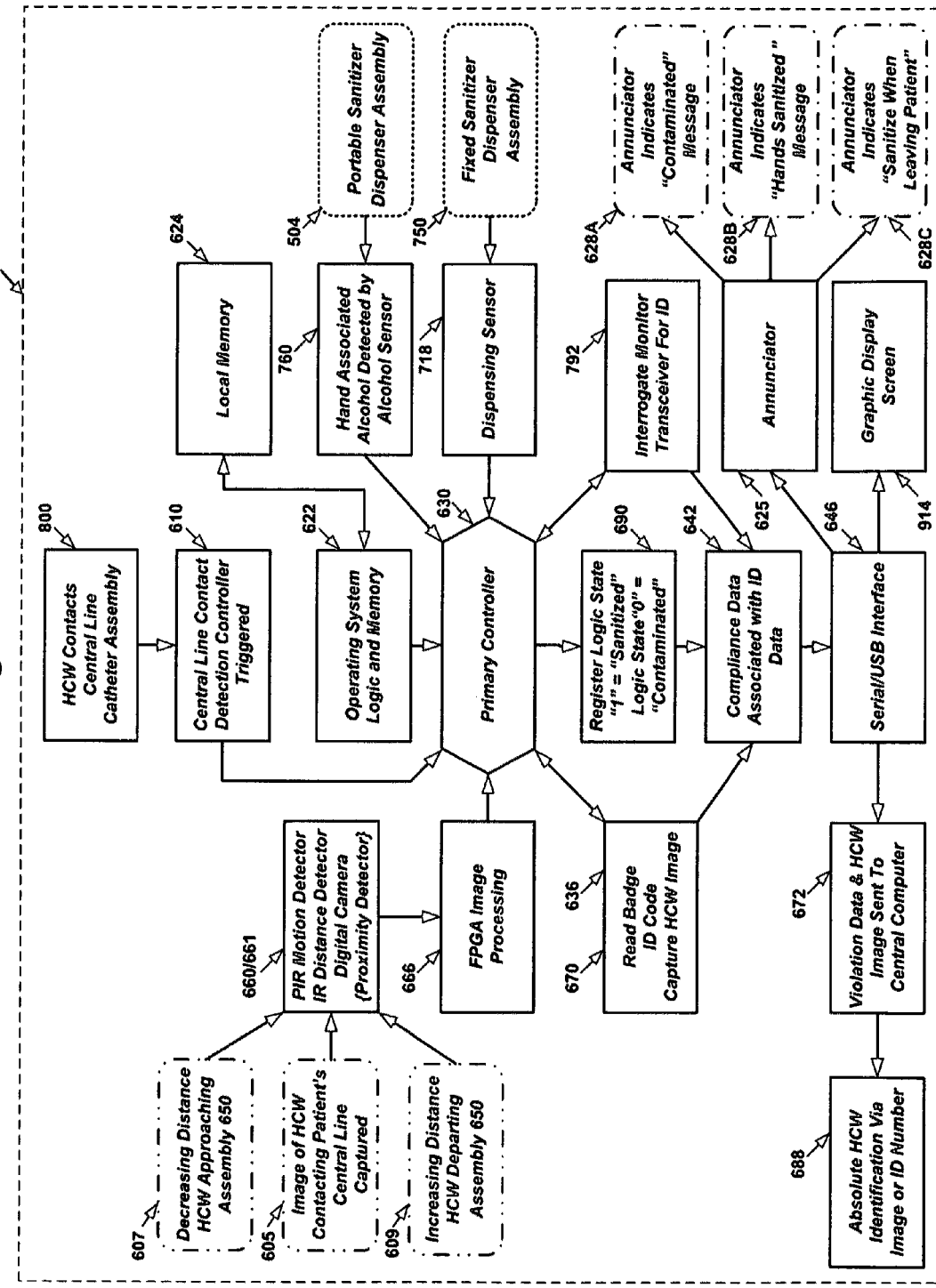
FIG. 25 is a flow diagram showing the interoperability of the components comprising a unified intravenous catheter monitoring assembly.

The configuration of the area contiguous to the fixed base sanitizer under observation by digital imaging device (s) 600 is such that the presence of a tracked HCW image 902 in such defined area concurrent with an electronic indication of that sanitizer's activation will be cause to indicate, and associate a logic "1" (sanitized) with the image 902 of the HCW 222 being electronically observed and tracked by digital imaging device 660 operatively associated with image processing firmware 638 in conjunction with operating system 622, is sanitized. While the electronic communication process is preferably accomplished via RF wireless means, IR transmissions utilizing IR transceivers may be utilized to achieve similar results. As discussed hereafter, the worker or visitor must preferably use a hand sanitizer associated with the patient or patient's room in order to avoid a warning signal when physically touching or approximating the patient's contact/proximity reactive intravenous catheter assembly 800. The aforementioned sanitizer(s) are preferably employed shortly before and in near proximity (preferably <2 meters) to, the intravenous assembly 800 as determined by digital imaging sensor 660 and operating system 622 such that its operation will minimize or avoid incidental contamination of HCW hands subsequent to utilizing the patient's associated sanitizer. The sanitizer is also preferably located in the patient control area 210 near the patient to minimize the possibility of contamination subsequent to sanitizing ones hands. The sanitizer activation switch 718 may be mechanical but is preferably a contactless capacitive or infrared sensor that, in addition to causing soap or other sanitizing material to be dispensed also causes the generation of an activation and identification signal 564. The hand sanitizer shown is a "bag-in-box" type dispenser that receives a bladder filled with soap or other sanitizing agent 736. It can alternatively be associated with a mechanical lever and electrical switch (not shown) that causes the compression of the soap-containing bag. In this manner, upon receipt of activation signal 564 from the sanitizer 700 the primary controller 600 may integrate the information regarding the hand sanitizing activity of the health care worker with the detected and tracked image 902 and ID number 904 of the HCW 222. Appropriate messages 628A, B and C may then be displayed on the associated annunciators. Contact with the patient's intravenous catheter assembly 800 with unsanitized hands, logic "0", may cause a warning signal to be generated or displayed on primary controller's 600 annunciator 626 or speaker 566. The system accordingly tracks and determines whether a particular HCW or visitor has sanitized their hands using a particular patient or patient area-associated sanitizer and updates compliancy information stored on memory 624 within primary controller 600. Such compliance, or lack of compliance, information may be shared by wired or wireless means 672 with an off-site data base 688 for absolute identification and recordation for compilation, to optionally include image recognition of the HCW and compilation of hygiene compliance behavior. Contact with or proximity to the patient's intravenous catheter assembly 800 resulting in the generation of a "sanitized" logic "1" HCW as determined by primary controller 600 will result in no announcement or may result in an annunciator indicating proper protocol compliance as determined by the primary controller as well as recordation of same. In the preferred embodiment, actuation of a sanitizer not specifically associated with the primary controller or outside of the patient control area 210 as determined by the image processing firmware 638 in conjunction with operating system 622 that is considered not to be appropriate activation associated with the patient 200 will be considered as none responsive by the primary controller and will be interpreted as if the worker has not sanitized their hands at all. This indication will result in their hygiene status remaining "contaminated" logic "0" and a violation will be noted by primary controller 600 if and when contact with the patient's intravenous catheter assembly 800 is determined by contact controller 610. The illustrative diagram FIG. 23 and the flow diagram FIG. 25 is representative of a consolidation of previously referred to components of a intravenous catheter monitoring system to include an alcohol detection assembly 760 designed to detect and indicate the presence of alcohol containing sanitizer on a HCW's hands, operatively associated and co-located within a single, portable, intravenous catheter monitoring system 100 assembly 650. Comprised of a primary controller 600, inclusive of a intravenous catheter contact sensor controller 610 operatively associated with a intravenous catheter contact assembly 800, a sanitizer dispenser 700, a motion and proximity detector as a PIR motion detector 661 or preferably a digital imaging device such as an integral, digital imaging sensor 660 with associated image tracking and processing routine 638, firmware 666 and IR illumination 664 and/or removably secured cooperating digital imaging sensor 660A, all co-located within a single assembly 650 whose physical structure is configured so as to be adaptable to be removable secured and co-located with a fluid containing IV bag 330 supported on an IV pole 316.

An exemplary assembly incorporates the functions of the aforementioned primary controller 600 with removable memory 624, on/off switch 654, a data bus port 646, badge QR ID reading sensor 670, a complete alcohol vapor sensing assembly 760 including 766, 772 and 762, a fixed sanitizer dispenser 700, mobile proximity/digital imaging sensor 660 with an optional IR LED illumination array 664, an optional additional cooperating digital imaging device 660A, a contact sensitive intravenous catheter assembly 800 associated with a contact detecting charge transfer controller 610 and associated sensitivity control 662. More specifically, electrode assembly 850 is operatively associated with a contact reactive intravenous catheter assembly 800 which is operatively associated with a fluid containing IV bag 310 and optionally, infusion pump 860 (FIG. 13 and FIG. 27). Electrode assembly 850 is electrically associated with charge transfer controller 610 and primary controller CPU 630 via electrical interface 830 and electrical connector 835. A display 626 with message 628A, B and C along with speaker 612 are provided to function as annunciators indicating HCW hygiene status and/or cautionary warnings. Dispensing sensor 718 which may be operated via touch, IR or mechanical means will activate a plunger or preferably a peristaltic dispensing mechanism associated with a reservoir 750 (not shown) that may accommodate a "bag in a box" liquid or gel sanitizer (not shown) so as to present sanitizing material at orifice 736. Activation of switch 718 also causes the generation of signal 564, receipt of this signal and subsequent validation of the associated identification number by the primary controller will cause the generation of a signal 560 to be transmitted to the associated the annunciators 526/626/726 resulting in the display of a "Sanitized" message 628B.

Figure 24:
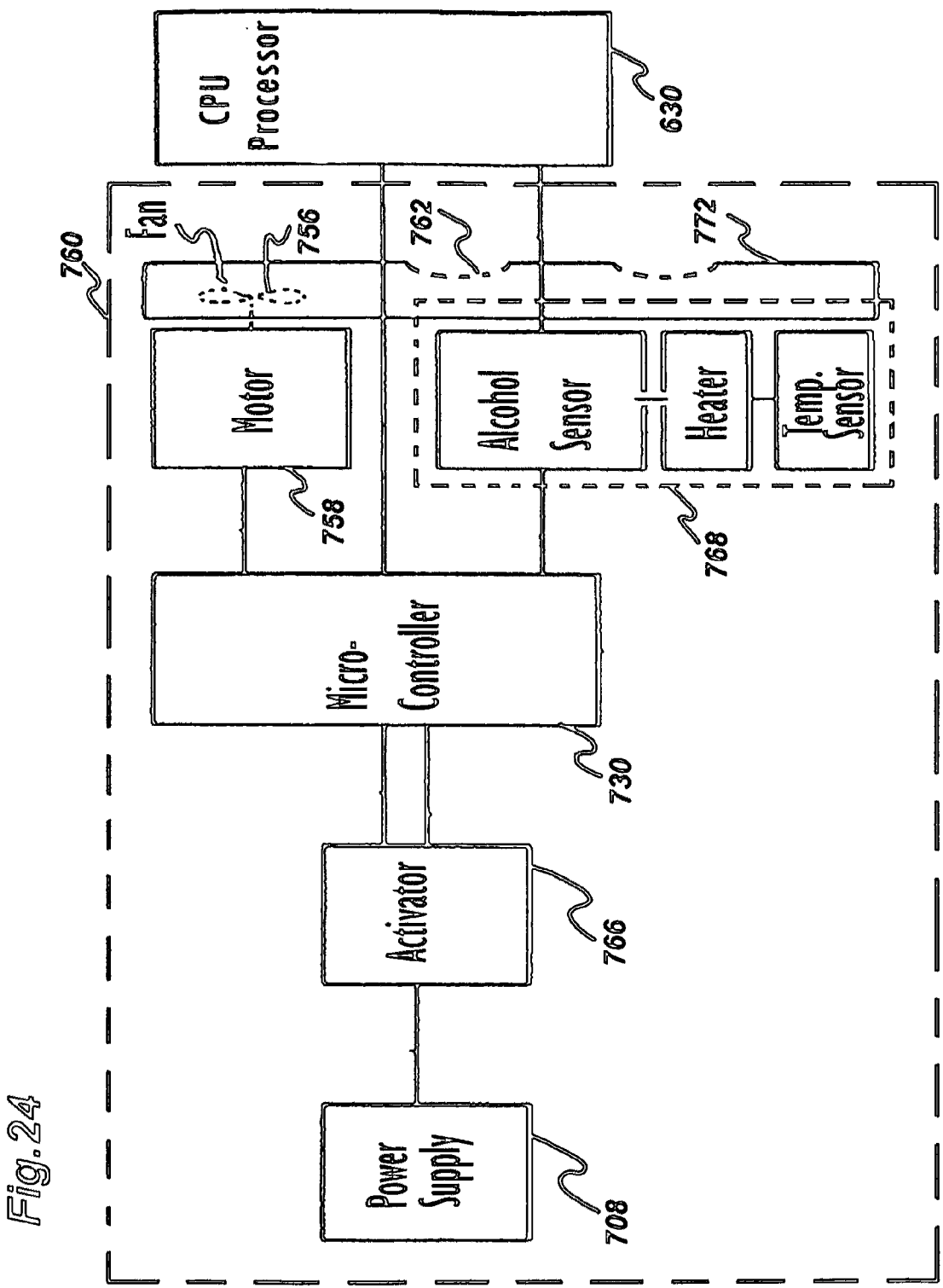
FIG. 24 is a schematic view of the alcohol sensing assembly to be used to detect alcohol containing hand sanitizer when used with a catheter hygiene monitoring system.

In anticipation that a non-system associated fixed or portable sanitizer dispenser 504 may be used in near proximity to the patient 200 to sanitize a Health Care Workers hands in lieu of dispensing sanitizer contained within assembly 650 from sanitizer dispensing port 736, hand detector 766 is configured to activate alcohol vapor or taggant detection assembly 760 to determine the presence of alcohol vapor on one or more hands placed below plenum 772 associated with alcohol sensor/detector 768. Detection of one or more hands by activator switch 766 causes power to be applied to a fan motor 758 and fan blade 756 operatively associated with a plenum 772 so as to cause alcohol vapors from the nearby and recently sanitized hands of the HCW to be drawn through induction port 762 of the plenum 772 to the surface of the now activated commercially available ethanol alcohol sensor 768 operatively associated with microcontroller 730. The detection of the presence of a specific level of alcohol vapor resulting from this activation would be indicative of recent hand sanitizing with alcohol containing sanitizer by the Health Care Worker. Alcohol detection assembly 760 as illustrated in FIG. 24 is designed to detect the presence of ethanol alcohol vapors, ethanol being a primary active ingredient in alcohol based sanitizer gels soaps or lotions, on the hands of a Health Care Worker, when presented to the detector assembly prior to the HCW's contact with a patient's intravenous catheter assembly 800. A positive indication of the presence of alcohol vapors or taggant on the HCW's hands when presented to induction port 762 associated with sensor 768 operatively associated with primary controller 600 would be indicative of recent hand sanitizing. Such detection would result in a logic signal "1" within the primary controller logic and CPU 630 along with the generation an annunciator message 628B indicating "sanitized" on the system associated annunciator 626.

When required, determination of the identity of the HCW operating the dispenser may be accomplished by one or more of the following methods; QR ID reading sensor 670 reading the HCW's ID badge 510 QR code, (QR code=quick response code) 578, digital imaging device 660/66A, digitizing and forwarding for storage the image of HCW's who is operating monitoring assembly prior to an image data base referencing of such image, wirelessly reading by encoder/decoder 636 of pre-recorded ID codes by interrogation of HCW monitor acquiring identifying information from the HCW's associated monitor via RF/IR transmission when the digital imaging sensor 660/661 and associated firmware or scanner 670 determines near proximity of the HCW to the patient. This identify information may be incorporated into a data log of hygiene compliance to include time, place, HCW and patient ID, sanitizing frequency and violation data to be stored locally in removable memory 624 or remotely via data port 646 operatively associated with a remote computer 688 via wired or wireless means 672. Operation of this embodiment may be described as follows;

When an approaching Health Care Worker 222 is detected in near proximity to assembly 650 (FIG. 23) via proximity detector which may be a PIR (not shown), scanner 670 or preferably a digital imaging sensor 660 associated with image processing firmware 640 functioning as a proximity detector which may be a associated with an image processing FPGA 666 configured to provide selective motion detection in its selective active field of view. When a HCW is determined to be approaching the patient and/or their intravenous catheter assembly 800 and is determined to be in near proximity (<2 meters) from assembly 800 or patient as determined by digital imaging device 660/660A, 661 or 670, annunciator 626 provides a cautionary message 628A indicating hand sanitizing is required before contact with the patient's intravenous catheter. Upon prompting by an audio message presented by speaker 612 and if the HCW has recently sanitized their hands with an alcohol containing sanitizer or soap, they may place their hands under hand detection sensor 766 activating the alcohol vapor detection assembly 760 so that alcohol vapors associated with the previously applied sanitizer may be detected as evidence of recent hand sanitizing per hygiene protocol. If however, the HCW has not recently sanitized their hands the HCW may elect to place their hands under dispensing sensor 718 thereby activating a dispensing mechanism that provides sanitizer via opening 736. Concurrent with the dispensing of sanitizer via opening 736 or the detection of alcohol vapors via induction port 762, on the hands of HCW via alcohol sensor 768 a logic code "1" is generated by primary controller CPU 630 and associated operating system 622 indicating hand sanitizing has been completed. When identification of the HCW attending to the patient and/or contacting the patient's intravenous catheter assembly 800 is required for institutional purposes, and identification has not been achieved via alternate means, described supra and without a logic level "1" indicating recent hand sanitizing has been accomplished as determined by primary controller 600, subsequent detection of contact with the patient's intravenous catheter 800 by HCW 222, as determined by electrode assembly 850 electrically associated with charge transfer controller 610 and primary controller CPU 630, will cause the generation of a warning indication 628A on annunciators 626 and/or 612 and recordation of the HCW image via digital imaging device 660 while noting the hygiene protocol violation to include time of violation, patient and HCW ID and/or station (650) ID. Such data, along with digital images from assembly's 650 digital imaging sensors 660/660A's whose field of view may be inclusive of imaging the patient's intravenous catheter assembly 800 and images identifying the HCW initiating such intravenous catheter contact reflecting hygiene protocol violation and compliance may be stored locally on memory 624 or transferred via wired or wireless means 672 to a remote computer 688 for identification, data compiling and processing.

Given the discussion thus far, a system is provided in accordance with a first exemplary embodiment that includes a catheter assembly 800 including one or more tubes (e.g. tubes 325) for conveying fluids. The system further includes a charge transfer proximity sensor assembly comprising an electrode (e.g. electrode 810) coupled to the catheter/IV assembly and a charge transfer controller circuit 610 electrically connected (e.g. by electrical connector 830 shown in FIG. 8) to the electrode. The charge transfer proximity sensor assembly is configured to detect contact or near contact (close proximity) by a person with the catheter assembly and generate an electrical signal responsive to such contact. The system may further include an annunciator (e.g. annunciator 626) configured to display a message following generation of the electrical signal by the charge transfer proximity sensor. One or more embodiments of the system further include a hand sanitizer (500, 700) configured for generating a signal evidencing use of the hand sanitizer and a controller 600 configured for processing the signals generated by the hand sanitizer and the charge transfer proximity sensor assembly. The controller is further configured to generate a signal signifying a non-compliant event when the electrical signal from the charge transfer proximity sensor assembly is not preceded by a signal from the hand sanitizer. In one or more further embodiments of the system, the charge transfer proximity sensor assembly is configured to detect a change in capacitance caused by the presence of a hand within twenty five centimeters or less of at least one portion of the catheter assembly. In one or more further embodiments of the system the electrode is within a lumen of the catheter assembly and therefore is able to contact liquid passing through the lumen. The catheter assembly, for example a central venous catheter assembly, includes a housing in fluid communication with the one or more tubes and an electrode comprising an elongate probe secured to the housing in an exemplary embodiment. In a further exemplary embodiment of the system, the controller is further configured to generate the signal signifying the non-compliant event when the signal from the hand sanitizer does not precede the signal from the charge transfer proximity sensor assembly by a predetermined time.

A system in accordance with a second exemplary embodiment includes a liquid source 310, such as shown in FIG. 2 and a catheter assembly including one or more tubes 325 for conveying fluid 330 and in fluid communication with the liquid source. The system further includes a controller 610 (FIG. 19), 840 (FIG. 26) electrically coupled to the catheter assembly, the controller being configured to detect a change in an electrical parameter resulting from a person's contact or near contact (close proximity) with the catheter assembly and generate a signal upon detection of the change in the electrical parameter. The system may further comprise an annunciator responsive to the signal from the controller. In one exemplary embodiment of the system, the catheter assembly includes an electrode 810, 810A in fluid communication with the liquid source, the controller 610 and electrode comprising a charge transfer proximity sensor assembly. Another exemplary embodiment of the system further includes an electrically conductive coil 834, at least one of the tubes of the catheter assembly passing through the electrically conductive coil, the controller being configured as an inductively reactive controller 840 electrically coupled to the coil 834. One or more further exemplary embodiments of the system further includes a hand sanitizer 500, 700 configured for generating a signal evidencing use of the hand sanitizer and a primary controller 600 configured for processing the signals generated by the hand sanitizer and the controller 610, 840, the primary controller being further configured to generate a signal signifying a non-compliant event when the electrical signal from the controller is not preceded by a signal from the hand sanitizer. Means such as an accelerometer 668 or digital imaging device may be employed in a further embodiment to determine whether the catheter assembly is in motion. This allows the system to automatically be placed in a standby mode.

A method in accordance with an exemplary embodiment includes detecting whether a person is within a selected area by using a digital imaging device 660, 660A, detecting whether an electrical signal has been generated by a hand sanitizer evidencing use of the hand sanitizer 500, 700 while the person is within the selected area, electronically detecting whether the person has made contact or near contact with a patient's catheter assembly 100, and generating a signal representing non-compliance if contact or near contact with the catheter assembly is electronically detected without prior generation of the electrical signal from the hand sanitizer. The selected area is proximate to the catheter assembly in an exemplary embodiment of the method. In a further exemplary embodiment of the method, the step of electronically detecting whether the person has made contact or near contact with a patient's catheter assembly is conducted using an electrode coupled to the catheter assembly and a charge transfer proximity sensor assembly electrically connected to the electrode.

Another exemplary method includes detecting contact or near contact with a patient's catheter assembly by a person via a charge transfer proximity sensor assembly, determining the hand hygiene status of the person, and generating a signal signifying hygienic non-compliance or compliance based on the hand hygiene status of the person and the detected contact or near contact with the patient's catheter assembly. The step of determining the hand hygiene status of the person further includes determining whether an electronic signal has been generated by a hand sanitizer in accordance with an exemplary embodiment of the method. In accordance with another exemplary embodiment of the method, the step of determining the hand hygiene status of the person further includes detecting the presence of alcohol vapor in the vicinity of the person's hand. One or more further embodiments of the method further include displaying a message based on the generated signal.

A method in accordance with a further exemplary embodiment includes detecting a change in an electrical parameter resulting from contact or near contact by a person with a catheter assembly connected to a patient for adding or removing fluids to/from the patient, and actuating an annunciator responsive to detection of the change in the electrical parameter. In another embodiment of the method, the catheter assembly includes an electrode contacting the liquid, and the step of detecting a change in an electrical parameter is conducted by a charge transfer sensor assembly (e.g. 610) electrically connected to the electrode. The method optionally further includes detecting a person in a selected area proximal to the catheter assembly and causing the annunciator to display a message following detection of the person in another exemplary embodiment. The method further includes 1) detecting whether an electrical signal has been generated by a hand sanitizer evidencing use of the hand sanitizer and 2) causing the annunciator to display a selected message if detection of a change in the electrical parameter precedes generation of the electrical signal by the hand sanitizer in another embodiment in another exemplary embodiment.

What is claimed is:

1. A system for monitoring hand hygiene compliance comprising:
   a catheter assembly associated with one or more tubes for conveying fluids;
   a charge transfer proximity sensor assembly comprising an electrode coupled to the catheter assembly; and
   a charge transfer controller circuit electrically connected to the electrode, the charge transfer proximity sensor assembly being configured to detect contact or close proximity by a person with the catheter assembly and generate an electrical signal for controlling an annunciator responsive to such contact; and
   a hand sanitizer electrically associated with the controller configured for generating a signal evidencing use of such sanitizer.

2. The system of claim 1, wherein the proximity sensor assembly is configured to detect a change in capacitance caused by the presence of a person within twenty five centimeters or less of at least one portion of the catheter assembly.

3. The system of claim 1, wherein at least part of the electrode is within a lumen of the catheter assembly.

4. The system of claim 1, further including a liquid within the lumen, the electrode contacting the liquid.

5. The system of claim 1, wherein the catheter assembly includes a housing in fluid communication with the one or more catheter tubes, the electrode comprising an electrical probe secured to the housing.

6. The system of claim 1, wherein the controller is further configured to generate the signal signifying a non-compliant event when the signal from the hand sanitizer evidencing use does not precede the signal from the charge transfer proximity sensor assembly indicating contact by a second person.

7. A system comprising:
   a catheter assembly including one or more tubes for conveying fluid and in fluid communication with a liquid source associated with a first person;
   a controller electrically coupled to the catheter assembly, the controller being configured to detect a change in an electrical parameter resulting from a second person's contact with or close proximity to the catheter assembly and generate a signal upon detection of the change in the electrical parameter; and
   a hand sanitizer operatively associated with the controller configured for generating a signal evidencing use of the hand sanitizer.

8. The system of claim 7, wherein the catheter assembly includes an electrode in fluid communication with the liquid source; the controller and electrode comprising a charge transfer proximity sensor assembly.

9. The system of claim 7 further including an electrically conductive coil, at least one of the tubes of the catheter assembly being electrically conductive when passing through the electrically conductive coil, the coil being reactive to contact with the catheter tube and the controller being configured as a reactive controller electrically coupled to the coil.

10. The system of claim 7, further including an annunciator operatively associated with the controller, the annunciator capable of indicating contact with the catheter assembly.

11. A method comprising:
    detecting a change in an electrical parameter of a fluid using a fixed or removably secured electrode in electrical contact with the fluid in a first person's catheter resulting from contact or near contact by a second person with the first person's catheter; and, detecting a change in the electrical parameter of the fluid using a sensor assembly electrically associated with the electrode.

12. The method of claim 11 further includes an annunciator responsive to detection of the change in the electrical parameter.

13. The method of claim 11, further including detecting whether an electrical signal has been generated by evidencing the use of an operatively associated sanitizer and causing an annunciator to display a selected message if detection of a change in the electrical parameter precedes generation of the electrical signal by means evidencing use of the sanitizer.

14. The method of claim 11, further including detecting whether an electrical signal has been generated by evidencing the use of an operatively associated sanitizer and causing an annunciator to display a selected message if detection of a change in the electrical parameter is subsequent to the generation of the electrical signal evidencing use of the hand sanitizer.

15. A system comprising:
    a fixed or removably secured electrode associated with a first person's fluid delivery catheter for detecting a change in an electrical parameter of the catheter resulting from contact or near contact by a second person with the catheter; and the electrode providing
    a means of causing the generation of an electrical control signal.

16. The system of claim 15, further including a means of causing an annunciator to display a selected message if detection of a change in the electrical parameter is determined to preceed the generation of the electrical control signal by means evidencing use of an operationally associated hand sanitizer.

* * * * *